(12) United States Patent
Refaeli et al.

(10) Patent No.: US 8,551,968 B2
(45) Date of Patent: Oct. 8, 2013

(54) METHODS FOR GENERATION OF ANTIBODIES

(75) Inventors: Yosef Refaeli, Denver, CO (US); Brian Curtis Turner, Denver, CO (US)

(73) Assignee: National Jewish Health, Denver, CO (US)

( * ) Notice: Subject to any disclaimer, the term of this patent is extended or adjusted under 35 U.S.C. 154(b) by 1140 days.

(21) Appl. No.: 12/048,148

(22) Filed: Mar. 13, 2008

(65) Prior Publication Data

US 2010/0279351 A1    Nov. 4, 2010

Related U.S. Application Data

(60) Provisional application No. 60/894,654, filed on Mar. 13, 2007, provisional application No. 60/939,042, filed on May 18, 2007.

(51) Int. Cl.
*A61K 48/00* (2006.01)
*C12N 15/00* (2006.01)

(52) U.S. Cl.
USPC ........................................ 514/44 R; 435/455

(58) Field of Classification Search
USPC ........................................ 514/44 R; 435/455
See application file for complete search history.

(56) References Cited

U.S. PATENT DOCUMENTS

| | | | |
|---|---|---|---|
| 5,476,996 A | 12/1995 | Wilson et al. | |
| 5,698,767 A | 12/1997 | Wilson et al. | |
| 5,811,301 A | 9/1998 | Cameron | |
| 5,824,837 A * | 10/1998 | Chen et al. | 800/3 |
| 5,849,288 A | 12/1998 | Reisner | |
| 7,135,287 B1 | 11/2006 | Lonberg et al. | |
| 7,311,920 B1 | 12/2007 | Devico et al. | |
| 7,582,745 B2 | 9/2009 | Sah et al. | |
| 7,767,453 B2 | 8/2010 | Zhang | |
| 2001/0049393 A1 | 12/2001 | Coller et al. | |
| 2003/0072794 A1 | 4/2003 | Boulikas | |
| 2005/0220705 A1 | 10/2005 | Brooks et al. | |
| 2005/0281816 A1 | 12/2005 | Lamping et al. | |
| 2006/0115898 A1 | 6/2006 | Zhang et al. | |
| 2006/0154331 A1 | 7/2006 | Avidan et al. | |
| 2006/0156422 A1 | 7/2006 | Dalrymple et al. | |
| 2007/0011753 A1 | 1/2007 | Ito et al. | |
| 2007/0067854 A1 | 3/2007 | Habu et al. | |
| 2007/0093420 A1 | 4/2007 | Yeomans et al. | |
| 2007/0116691 A1 * | 5/2007 | Cambier et al. | 424/93.21 |
| 2007/0130628 A1 * | 6/2007 | Brown | 800/6 |
| 2007/0248618 A1 | 10/2007 | Cohen | |
| 2009/0291094 A1 | 11/2009 | Refaeli et al. | |
| 2010/0047217 A1 | 2/2010 | Refaeli et al. | |
| 2010/0055129 A1 | 3/2010 | Refaeli et al. | |

FOREIGN PATENT DOCUMENTS

| | | | |
|---|---|---|---|
| EP | 1 103 615 A1 * | 5/2001 | |
| EP | 1103615 | 5/2001 | |
| EP | 1357184 A2 | 10/2003 | |
| EP | 1792627 A1 | 6/2007 | |
| GB | 2387599 | * 10/2003 | |
| JP | 2005-527211 A | 9/2005 | |
| WO | 94/04686 A1 | 3/1994 | |
| WO | 94/19465 A2 | 9/1994 | |
| WO | WO-98-10058 | 3/1998 | |
| WO | WO-99-53028 | 10/1999 | |
| WO | WO-00-09669 | 2/2000 | |
| WO | 00/62067 A1 | 10/2000 | |
| WO | 01/38548 A2 | 5/2001 | |
| WO | 03/089630 A1 | 10/2003 | |
| WO | WO 03/008630 | * 10/2003 | |
| WO | 2005/014785 A2 | 2/2005 | |
| WO | WO-2006-032876 | 3/2006 | |
| WO | 2006/116512 A1 | 11/2006 | |
| WO | 2007/047583 A2 | 4/2007 | |
| WO | 2007/067183 A1 | 6/2007 | |
| WO | 2009/139930 A2 | 11/2009 | |

OTHER PUBLICATIONS

Refaeli et al (Proc Nat Acad Sci 102(11): 4097-4102, 2005).*
Eischen et al., 2001, Molecular Cell Biology, 21: 5063-5070.*
EP 08743862 Supplementary Search Report dated Feb. 9, 2010.
PCT/US08/56896 Written Opinion dated Jul. 18, 2008.
PCT/US08/56896 International Preliminary Report on Patentability dated Sep. 15, 2009.
EP08743862 Office Action dated May 14, 2010.
Habib, T., "Myc stimulates B lymphocyte differentiation and amplifies calcium signaling," J.Cell Biol. 179(4):717-731 (2007).
Hiramatsu, H., "Complete reconstitution of human lymphocytes from cord blood CD34+ cells using the NOD/SCID/gammacnull mice model," Blood 102(3):873-880 (2003).
Huang, C.Y., "Dynamic regulation of c-Myc proto-oncogene expression during lymphocyte development revealed by a GFP-c-Myc knock-in mouse," Eur. J. Immunol. 38(2):342-349 (2008).
Littlewood, T.D., "A modified oestrogen receptor ligand-binding domain as an improved switch for the regulation of heterologous proteins," Nucleic Acids Res. 23(10:1686-1690 (1995).
Refaeli, Y., "The B cell antigen receptor and overexpression of MYC can cooperate in the genesis of B cell lymphomas," PLOS Biol. 6(6),e152:1208-1225 (2008).
Young, et al., "B-cell receptor signaling in the genesis and maintenance of B-cell lymphoma," Future Oncology 4(5):591-594 (2008).
PCT/US09/03105 Search Report dated Jan. 15, 2010.
Podsypanina, K. et al., "Oncogene cooperation in tumor maintenance and tumor recurrence in mouse mammary tumors induced by MYC and mutant Kras," PNAS 105(13):5242-5247 (2008).
Refaeli, Y. et al., "The protooncogene MYC can break B cell tolerance," PNAS 102(11):4097-4102 (2005.
Roh, M. et al., "Transgenic Mice for Cre-Inducible Overexpression of the Oncogenes c-MYC and Pim-1 in Multiple Tissues," Genesis 44:447-453 (2006).

(Continued)

Primary Examiner — Marcia S. Noble
Assistant Examiner — Magdalene Sgagias
(74) Attorney, Agent, or Firm — Morrison & Foerster LLP

(57) ABSTRACT

This invention generally relates to methods for the production of antibody producing cells and antibodies in protooncogene expressing animals. The invention also relates to methods for the efficient production of antibodies specific for antigens that are normally subject to immunological constraints such as self tolerance. The invention further relates to the production of antibody producing cells and antibodies without the need for the conventional fusing of antibody producing B cells with a myeloma fusion partner.

12 Claims, 9 Drawing Sheets

(56) References Cited

OTHER PUBLICATIONS

Schmidt, E.V. et al., "Transgenic mice bearing the human c-*myc* gene activated by an immunoglobulin enhancer: A pre-B-cell lymphoma model," PNAS USA 85:6047-6051 (1988).
PCT/US08/56896 Search Report dated Aug. 14, 2008.
Office Action received for Korean Patent Application No. 10-2009-7021320, mailed on Jul. 29, 2011, 7 pages (3 pages of English Translation and 4 pages of Office Action).
Office Action received for European Patent Application No. 08743862.8, mailed on Sep. 23, 2010, 6 pages.
Bunting et al., "Restoration of lymphocyte function in Janus kinase 3-deficient mice by retroviral-mediated gene transfer," Nature Medicine 4:58-64 (1998).
Chadwick et al., "Notch Signaling Induces Apoptosis in Primary Human CD34+ Hematopoietic Progenitor Cells," Stem Cells 25:203-210 (2007).
Cheng et al., "BCL-2, BCL-$X_L$ Sequester BH3 Domain-Only Molecules Preventing BAX- and BAK-Mediated Mitochondrial Apoptosis," Mol Cell 8:705-711 (2001).
Conti, L. et al., "Gene therapy using neural stem cells," Methods Mol. Biol. 198:233-244 (2002).
DeoCampo et al., "Cooperation of bcl-2 and myc in the neoplastic transformation of normal rat liver epithelial cells is related to the down-regulation of gap junction-mediated intercellular communication," Carcinogenesis 21(8):1501-1506 (2000).
Eilers, M. et al., "Chimeras of Myc Oncoprotein and Steroid Receptors Cause Hormone-Dependent Transformation of Cells," Nature 340(6228):66-68 (1989).
Eischen et al., "Apoptosis Triggered by Myc-Induced Suppression of Bcl-$X_L$ or Bcl-2 is Bypassed during Lymphomagenesis," Mol Cell Biol 21:5063-5070 (2001).
Esdar, C. et al., "Differentiation-associated apoptosis of neural stem cells is effected by Bcl-2 overexpression: impact on cell lineage determination," Eur. J. Cell Biol. 80(8):539-553 (2001).
Felsher and Bishop, "Reversible Tumorigenesis by *MYC* in Hematopoietic Lineages," Mol Cell 4:199-207 (1999).
Gauss, "DEAE-dextran enhances electroportation of mammalian cells," Nucl Acids Res 20(24):6739-6740 (1992).
Guzman et al., "Preferential induction of apoptosis for primary human leukemic stem cells," PNAS 99(25):16220-16225 (2002).
Hoffman, "Progress in the development of systems in vitro expansion of human hematopoietic stem cells," Curr Op Hematology 6(3):14 pages (1999).
Horton, S.J. et al., "Continuous MLL-ENL expression is necessary to establish a "Hox Code" and maintain immortalization of hematopoietic progenitor cells," Cancer Res. 65(20):9245-9252 (2005).
Hoshimaru, M. et al., "Differentiation of the immortalized adult neuronal progenitor cell line HC2S2 into neurones by regulatable suppression of the V-MYC oncogene," Proceedings of the National Acadamy of Sciences of USA 93(4):1518-1523 (1996).
Howard, M.J. et al., "Transplantation of apoptosis-resistant embryonic stem cells into the injured rat spinal cord," Somatosensory & Motor Research 22(1-2):37-44 (2005).
Korbling et al., "Allogeneic Blood Stem Cell Transplantation: Peripheralization and Yield of Donor-Derived Primitive Hematopoietic Progenitor Cells (CD34+ Thy-1$^{dim}$) and Lymphoid Subsets, and Possible Predictors of Engraftment and Graft-Versus-Host Disease," Blood 86:2842-2848 (1995).
Krosl et al., "In vitro expansion of hematopoietic stem cells by recombinant TAT-HOXB4 protein," Nature Med 9(11):1428-1432 (2003).
McCarthy, "Underground movement," Nature Reviews Cancer 7:1 page (2007).
MacPherson, P. et al., "Activity-dependent gene regulation in conditionally-immortalized muscle precursor cell lines," J. Cell. Biol. 91(4):821-839 (2004).
Melkonyan et al., "Electroporation efficiency in mammalian cells is increased by dimethyl sulfoxide (DMSO)," Nucl. Acids Res. 24:4356-4357 (1996).
Miller et al., "Expansion in vitro of adult murine hemapoietic stem cells with transplantable lympho-myeloid reconstituting ability," PNAS USA 94:13648-13653 (1997).
Mooslehner et al., "Retroviral Integration Sites in Transgenic Mov Mice Frequently Map in the Vicinity of Transcribed DNA Regions," J Virol 64:3056-3058 (1990).
Moore et al., "In Vitro Maintenance of Highly Purified, Transplantable hematopoietic Stem Cells," Blood 89(12):4337-4347 (1997).
Pierelli et al., "Modulation of bcl-2 and p27 in human primitive proliferating hematopoietic progenitors by autocrine TGF-β1 is a cell cycle-independent effect and influences their hematopoietic potential," Blood 95:3001-3010 (2000).
Pinto et al., "Hematopoietic progenitor/stem cells immortalized by Lhx2 generate functional hematopoietic cells in vivo," Blood 99(11):3939-3946 (2002).
Pollock, K. et al., "A conditionally immortal clonal stem cell line from human cortical neuroepithelium for the treatment of ischemic stroke," Exp. Neurology 199(1):143-155 (2006).
Raymon, H.K. et al., "Immortalized human dorsal root ganglion cells differentiate into neurons with nociceptive properties," J. Neuroscience 19(13):5420-5428 (1999).
Richter et al., "Lhx2 expression in hematopoietic progenitor/stem cells in vivo causes a chronic myeloproliferative disorder andaltered globin expression," J Hematology 88(12):1336-1347 (2003).
Rosenwald et al., "Increased expression of eukaryotic translation initiation facots elF-4E and elF-2alpha in response to growth induction by c-myc," PNAS USA 90:6175-6178 (1993).
Sauer, "Inducible Gene Targeting in Mice Using the Cre/*lox* System," Methods: A Comparison to Methods in Enzymology 14:381-392 (1998).
Schroy and Todd, "A Simple Method for Freezing and Thawing Cultured Cells," Methods in Cell Science 2:309-310 (1976).
Schwarze et al., "Protein transduction: unrestricted delivery into all cells?" Trends in Cell Biology 10:290-295 (2000).
Sipone, S. et al., "Modeling brain pathologies using neural stem cells," Methods Mol. Biol. 198:245-262 (2002).
Takahashi et al., "Induction of Pluripotent Stem Cells from Mouse Embryonic and Adult Fibroblast Cultures by Defined Factors," Cell 126:663-676 (2006).
Tsai et al., "Lymhohematopoietic progenitors immortalized by a retroviral vector harboring a dominant-negative retinoic acid receptor can recapitulate lymphoid, myeloid, and erythroid development," Genes & Dev. 8:2831-2841 (1994).
Varnum-Finney et al., "Pluripotent, cytokine-dependent, hematopoietic stem cells are immortalized by constitutive Notch 1 signaling," Nature Medicine 6(11):1278-1281 (2000).
Vaux et al., "Bcl-2 gene promotes heamopoietic cell survival and cooperates with c-myc to immortalize pre-B cells," Nature 335:440-442 (1988).
Wang et al., "Primitive Human Hematopoietic Cells are Enriched in Cord Blood Compared With Adult Bone Marrow or Mobilized Peripheral Blood as Measured by the Quantitative In Vivo SCID-Repopulating Cell Assay," Blood 89:3919-3924 (1997).
Wikipedia [online], 2008, [retrieved on Nov. 13, 2008], Retrieved from Internet: URL:http://en.wikipedia.org/wiki/Stem_cell, pp. 1-11.
Wilson et al., "c-Myc controls the balance between hematopoietic stem cell self-renewal and differentiation," Genes and Development 18:2474-2763 (2007).
Wurm and Bernard, "Large-scale transient expression in mammalian cells for recombinant protein production," Curr Op Biotech 10:156-159 (1999).
Yanai et al., "A novel stromal cell-dependent hematopoietic cell line established from temperature-sensitive SV40 T-antigen transgenic mice," Exp Hematology 27:1087-1096 (1999).
PCT/US06/40379 Search Report dated Apr. 23, 2008.
PCT/US06/40379 Search Report and Written Opinion mailed Sep. 24, 2007.
EP 06826025 Supplementary Search Report dated Jul. 28, 2009.
U.S. Appl. No. 11/583,970 Office Action mailed Nov. 4, 2009.
U.S. Appl. No. 11/583,970 Office Action mailed Mar. 23, 2009.
U.S. Appl. No. 11/583,970 Office Action mailed Nov. 26, 2008.
U.S. Appl. No. 11/583,970 Office Action mailed Mar. 12, 2008.

(56) References Cited

OTHER PUBLICATIONS

U.S. Appl. No. 12/467,957 Office Action mailed Feb. 28, 2011.
U.S. Appl. No. 12/467,957 Office Action mailed Oct. 13, 2010.
Office Action received for Australian Patent Application No. 2009285547, mailed on Jul. 25, 2011, 2 pages.
Extended European Search Report received for European Patent Application No. 09800871.7, mailed on Jun. 24, 2011, 5 pages.
Extended European Search Report received for European Patent Application No. 09810692.5, mailed on Jul. 11, 2011, 5 pages.
Office Action received for Israel Patent Application No. 208810, mailed on Nov. 2, 2011, 3 pages of English Translation only.
Office Action received for Israel Patent Application No. 209343, mailed on Nov. 2, 2011, 3 pages of English Translation only.
Office Action received for Israel Patent Application No. 209968, mailed on Nov. 2, 2011, 3 pages of English Translation only.
International Preliminary Report on Patentability received for PCT Patent Application No. PCT/US2006/040379, mailed on Apr. 23, 2008, 5 pages.
International Search Report and Written Opinion received for PCT Patent Application No. PCT/US2008/082263, mailed on Jun. 25, 2009, 8 pages.
International Search Report and written Opinion Received for PCT Patent Application No. PCT/US2009/051242, mailed on Feb. 19, 2010, 9 pages.
International Preliminary Report on Patentability received for PCT Patent Application No. PCT/US2008/082263, issued on May 4, 2010, 6 pages.
International Search Report and Written Opinion received for PCT Patent Application No. PCT/US2009/055443, mailed on Jun. 30, 2010, 11 pages.
International Preliminary Report on Patentability Received for Application No. PCT/US2009/003105, mailed on Nov. 17, 2010, 6 pages.
International Preliminary Report on Patentability received for PCT Patent Application No. PCT/US2009/051242, mailed on Feb. 3, 2011, 7 pages.
International Preliminary Report on Patentability received for PCT Patent Application No. PCT/US2009/055443, issued on Mar. 10, 2011, 7 pages.
Non Final Office Action received for U.S. Appl. No. 12/962,197, mailed on Aug. 26, 2011, 20 pages.
Non-Final Office Action received for U.S. Appl. No. 12/550,166, mailed on Jan. 11, 2012, 24 pages.
Berkson et al., "Pilot Screening Programme for Small Molecule Activators of p53", International Journal of Cancer, vol. 115, 2005, pp. 701-710.
Caron et al., "Endosome Disruption Enhances the Functional Nuclear Delivery of Tat-Fusion Proteins", Biochemical and Biophysical Research Communications, vol. 319, 2004, pp. 12-20.
Carotta et al., "Directed Differentiation and Mass Cultivation of Pure Erythorid Progenitors from Mouse Embryonic Stem Cells", Blood, vol. 104, No. 6, Sep. 15, 2004, pp. 1873-1880.
Chen et al., "Small-Molecule Anthracene-Induced Cytotoxicity and Induction of Apoptosis through Generation of Reactive Oxygen Species", Biological & Pharmaceutical Bulletin, vol. 27, No. 6, Jun. 2004, pp. 838-845.
Coller et al., "Expression Analysis with Oligonucleotide Microarrays Reveals that MYC Regulates Genes Involved in Growth, Cell Cycle, Signaling, and Adhesion", Proc. Natl. Acad. Sci. USA, vol. 97, No. 7, Mar. 28, 2000, pp. 3260-3265.
Dang et al., "Identification of the Human c-myc Protein Nuclear Translocation Signal", Molecular and Cellular Biology, vol. 8, No. 10, Oct. 1988, pp. 4048-4054.
Kelso et al., "Survival of the Myeloid Progenitor Cell Line FDC-P1 is Prolonged by Interferon-α or Interleukin-4", Growth Factors, vol. 6, No. 3, 1992, pp. 233-242.
Qin et al., "Nuclear Factor κB Nuclear Translocation Upregulates c-Myc and p53 Expression during NMDA Receptor-Mediated Apoptosis in Rat Striatum", The Journal of Neuroscience, vol. 19, No. 10, May 15, 1999, pp. 4023-4033.
Radhakrishnan et al., "A Novel Transcriptional Inhibitor Induces Apoptosis in Tumor Cells and Exhibits Antiangiogenic Activity", Cancer Research, vol. 66, No. 6, Mar. 15, 2006, pp. 3264-3270.
Office Action received for Israel Patent Application No. 200919, mailed on Dec. 5, 2011, 2 pages of English Translation only.
Office Action received for Chinese Patent Application No. 200980126312.4, mailed on Jan. 30, 2012, 14 pages ( 7 pages of English translation and 7 pages of Office Action).
Office Action received for Chinese Patent Application No. 200980126312.4, issued on Aug. 28, 2012, 12 pages (6 pages of English Translation and 6 pages of Office Action).
Office Action received for Korean Patent Application No. 10-2009-7021320, mailed on Sep. 18, 2012, 11 pages (7 pages of English Translation and 4 pages of Office Action).
Office Action received for Israel Patent Application No. 209343, mailed on Aug. 14, 2012, 4 pages.
Office Action received for Israel Patent Application No. 209968, mailed on Aug. 21, 2012, 4 pages (2 pages of English Translation and 2 pages of Office Action).
Office Action received for Chinese Patent Application No. 200880015602.7, issued on Oct. 31 2012, 10 pages (6 pages of English Translation and 4 pages of Chinese Office Action).
Office Action received for Canadian Patent Appliication No. 2,735,522, mailed on Sep. 10, 2012, 3 pages.
Office Action received for Chinese Patent Application No. 200980127166.7, issued on Dec. 5, 2012, 3 pages.
Office Action received for Chinese Patent Application No. 200880015602.7, mailed on Jan. 31, 2012, 16 pages (10 pages of English translation and 6 pages of Office Action).
Office Action received for European Patent Application No. 09810692.5, mailed on Mar. 28, 2012, 3 pages.
Non Final Office Action Received for U.S. Appl. No. 12/506,894, mailed on Apr. 27, 2012, 34 pages.
Final Office Action Received for U.S. Appl. No. 12/550,166, mailed on May 11, 2012, 12 pages.
Oral Proceeding received for European Patent Application No. 08743862.8, mailed on May 14, 2012, 6 pages.
Extended European Search Report received for European Patent Application No. 09747016.5, mailed on May 30, 2012, 8 pages.
Office Action received for Japanese Patent Application No. 2009-553785, mailed on Jun. 19, 2012, 6 pages (2 pages of English Translation and 4 pages of Office Action).
Ju et al., "Anti-Apoptotic Therapy with a Tat Fusion Protein Protects Against Excitotoxic Insults in Vitro and in Vivo", Experimental Neurology, vol. 210, 2008, pp. 602-607.
Australian Search Report and Written Opinion received for Singapore Patent Application No. 201101367-9, mailed on Mar. 23, 2012, 17 pages.
Office Action received for Canadian Patent Application No. 2731767, mailed on Jul. 25, 2012, 3 pages.

* cited by examiner

Phenotype of TBLK-6 and TBLK-7

TBLK-6          TBLK-7

Approach #1: single retrovirus

Approach #2: two retroviruses for each Ig chain

METHODS FOR GENERATION OF ANTIBODIES

CROSS-REFERENCE TO RELATED APPLICATIONS

This application claims the benefit of priority under 35 U.S.C. §119(e) of U.S. Provisional Application No. 60/894,654, filed Mar. 13, 2007, and U.S. Provisional Application No. 60/939,042, filed May 18, 2007. The entire disclosure of each application is incorporated herein by reference for all purposes.

FIELD OF THE INVENTION

This invention generally relates to methods for the production of antibody producing cells and antibodies in protooncogene expressing animals. The invention also relates to methods for the efficient production of antibodies specific for antigens that are normally subject to immunological constraints such as self tolerance. The invention further relates to the production of antibody producing cells and antibodies without the need for the conventional fusing of antibody producing B cells with a myeloma fusion partner.

BACKGROUND OF THE INVENTION

The use of antibodies, particularly monoclonal antibodies, has revolutionized several areas of basic and clinical research as well as routine diagnostic procedures. The clinical application of monoclonal antibodies has emerged as a major new source of drugs for cancer therapy. For example, antibodies to a surface protein called CD20 have dramatically improved the prognosis of NHL patients, as well as for those with antibody-mediated autoimmune diseases.

The development of high titers of neutralizing antibodies has been correlated with the ability of patients to fight off many viral infections. The recent spread of avian flu in South East Asia showed that those individuals who survived infections were also those people who were able to mount an effective B-cell antibody-dependent neutralizing response. Similar findings were shown a year earlier in the case of SARS survivors. It is estimated that the annual death toll in the United States that is caused by influenza amounts to 30,000 to 50,000 people annually. The global death toll from influenza is estimated to be 20 to 30 times higher that the figures for the US alone. The two populations who are especially vulnerable are young children and the elderly. The development of neutralizing antibodies that could be provided passively would dramatically decrease the mortality caused by influenza or other viruses, such as HIV.

As of May 2005, there were 18 therapeutic monoclonal antibody products on the US market. Worldwide, there were an estimated 500 monoclonal antibody products in development by more than 200 companies for the treatment of virtually every debilitating disease. Approximately 80 of these monoclonal antibody products are in clinical trials. The global market for monoclonal antibodies is projected to increase to $16.7 billion in 2008.

The traditional approaches to generate monoclonal antibodies rely on the hyperimmunization of mice, or other animals of choice. The antibody producing cells from the spleen are then collected and fused to a myeloma cell fusion partner. The selection for cells that retain their antibody production gene is accomplished by a forward and reverse selection procedure. While this has proven to be a very powerful technique, the limitations imposed by basic biology likely result in a loss of >90% of all the possible specificities that could be obtained. Some of those limitations involve a mechanism called "self-tolerance", as well as certain requirements needed to attain a successful fusion between an antibody producing cell and a myeloma fusion partner.

Therefore, there is a need in the art for improved methods of generating antibodies that solve the problems related to the limitations listed above and lower the amount of time required to identify antibodies of interest.

SUMMARY OF THE INVENTION

One aspect of the invention relates to a method for producing an antibody producing cell by introducing an animal that inducibly overexpresses MYC to an antigen under conditions in which MYC is not overexpressed in the animal, recovering a B cell from the animal, and culturing the B cell under conditions in which MYC is overexpressed.

In some embodiments, the method further comprises a step of maintaining the animal under conditions in which MYC is overexpressed in the animal after the step of introducing the animal to the antigen.

In some embodiments, the animal inducibly overexpresses MYC predominantly in the B cells of the animal.

In some embodiments, the animal is an MMTV-rtTA/TRE-MYC mouse.

In some embodiments, the step of introducing the animal to the antigen comprises genetically transferring DNA encoding the antigen into the animal.

In some embodiments, the antigen comprises an autoantigen.

In some embodiments, the animal further expresses the antigen.

In some embodiments, the antigen comprises an HIV protein such as gp120 or gp41.

In some embodiments, the antigen comprises an antigen from an influenza virus such as hemagglutinin.

In some embodiments, the mouse is maintained on an antibiotic that represses MYC expression during the step of introducing the animal to the antigen, and the step of culturing the B cell is conducted in the absence of the antibiotic to produce an antibody producing cell.

In some embodiments, the method further comprises a step of removing the mouse from exposure to the antibiotic after the step of introducing the animal to the antigen.

In some embodiments, the antibiotic is doxycycline.

Another aspect of the invention relates to a method for producing an antibody by introducing an animal that inducibly overexpresses MYC to an antigen under conditions in which MYC is not overexpressed in the animal, recovering a B cell from the animal, culturing the B cell under conditions in which MYC is overexpressed, and recovering the antibody from the B cell culture.

In some embodiments, the method further comprises a step of maintaining the animal under conditions in which MYC is overexpressed in the animal after the step of introducing the animal to the antigen.

In some embodiments, the animal inducibly overexpresses MYC predominantly in the B cells of the animal.

In some embodiments, the animal is an MMTV-rtTA/TRE-MYC mouse.

In some embodiments, the step of introducing the animal to the antigen comprises genetically transferring DNA encoding the antigen into the animal.

In some embodiments, the antigen comprises an autoantigen.

In some embodiments, the animal further expresses the antigen.

In some embodiments, the antigen comprises an HIV protein such as gp120 or gp41.

In some embodiments, the antigen comprises an antigen from an influenza virus such as hemagglutinin.

In some embodiments, the antibody is a humanized antibody.

Another aspect of the invention relates to a method for producing an antibody by introducing a nucleic acid molecule encoding a VDJ joint region of a heavy or light chain gene of a B-cell into bone marrow-derived stem cells from an animal that inducibly overexpresses MYC and contains a genetic modification that prevents the production of B-cells, transferring the bone marrow-derived stem cells into a recipient animal, recovering a B cell from the recipient animal, culturing the B cell under conditions in which MYC is overexpressed, and recovering the antibody from the B cell culture.

In some embodiments, the method further comprises a step of maintaining the recipient animal under conditions in which MYC is overexpressed in the recipient animal after the step of transferring the bone marrow-derived stem cells into the recipient animal.

In some embodiments, the method further comprises a step of maintaining the recipient animal under conditions in which MYC is not overexpressed in the recipient animal after the step of transferring the bone marrow-derived stem cells into the recipient animal.

In some embodiments, the B cell from the first step is a human B cell.

In some embodiments, the B cell is isolated from a human.

In some embodiments, the human suffers from an antibody-mediated autoimmune disease.

In some embodiments, the first step comprises retrovirally transducing the bone marrow-derived stem cells with the nucleic acid molecule encoding a VDJ joint region.

In some embodiments, the nucleic acid molecule encoding the VDJ joint region is cloned from an isolated human B cell that selectively binds to an antigen of interest.

In some embodiments, the nucleic acid molecule encoding the VDJ joint region is a PCR-amplified fragment of a rearranged VDJ region from IgH and IgL sequences found in B cells obtained from a human donor.

In some embodiments, the human donor is selected from the group consisting of: a healthy donor and a patient that has an antibody-mediated autoimmune disease.

In some embodiments, the bone marrow-derived stem cells are further transduced with a nucleic acid molecule encoding a human IgH and a nucleic acid molecule encoding human IgL.

In some embodiments, the nucleic acid molecule encoding the human IgH and the nucleic acid molecule encoding the human IgL are the same nucleic acid molecule.

In some embodiments, one or both nucleic acid molecules encoding the human IgH and the human IgL are the same nucleic acid molecule that encodes the VDJ region.

In some embodiments, the bone marrow-derived stem cells are from a human or from a mouse.

In some embodiments, the mouse is an MMTV-rtTA/TRE-MYC mouse that contains a genetic modification is selected from the list consisting of: Rag-2$^{-/-}$, SCID, DNA-PK$^{-/-}$, Ku70$^{-/-}$, Ku80$^{-/-}$, XRCC4$^{-/-}$ and µMT$^{-/-}$.

In some embodiments, the recipient animal is a lethally irradiated mouse.

In some embodiments, the recipient animal is a SCID mouse.

In some embodiments, the animal is introduced in vivo to the antigen to which the VDJ region selectively binds.

In some embodiments, the antibody isotype is IgA or IgG.

In some embodiments, the Fc region of the antibody has been genetically modified to minimize the ability of the antibody to trigger autoimmune reactions and related immune-complex deposition problems.

Another aspect of the invention relates to a method for producing an antibody producing cell comprising by introducing an animal that inducibly overexpresses a protooncogene that promotes cell survival and proliferation to an antigen under conditions in which the protooncogene is not overexpressed in the animal, recovering a B cell from the animal and culturing the B cell under conditions in which the protooncogene is overexpressed.

Another aspect of the invention relates to a method for producing an antibody by introducing an animal that inducibly overexpresses protooncogene that promotes cell survival and proliferation to an antigen under conditions in which the protooncogene is not overexpressed in the animal, recovering a B cell from the animal, culturing the B cell under conditions in which the protooncogene is overexpressed, and recovering the antibody from the B cell culture.

Another aspect of the invention relates to a method for producing an antibody by introducing a nucleic acid molecule encoding an antigen into bone marrow-derived stem cells from an animal that inducibly overexpresses a protooncogene that promotes cell survival and proliferation, transferring the bone marrow-derived stem cells into a recipient animal, maintaining the recipient animal under conditions in which the protooncogene is overexpressed in the animal, recovering a B cell from the recipient animal, culturing the B cell under conditions in which the protooncogene is overexpressed and recovering the antibody from the B cell culture.

Another aspect of the invention relates to a method for producing an antibody by: introducing a nucleic acid molecule encoding a protooncogene that promotes cell survival and proliferation into bone marrow-derived stem cells from an animal, transferring the bone marrow-derived stem cells into a recipient animal, recovering a B cell from the recipient animal, introducing a nucleic acid molecule encoding an antigen into the B cell, culturing the B cell under conditions in which the protooncogene is overexpressed, and recovering the antibody from the B cell culture.

Another aspect of the invention relates to a method for producing an antibody by introducing a nucleic acid molecule encoding a protooncogene that promotes cell survival and proliferation into bone marrow-derived stem cells from an animal, transferring the bone marrow-derived stem cells into a first recipient animal, recovering a B cell from the first recipient animal, introducing a nucleic acid molecule encoding an antigen into the B cell, transferring the B cell into a second recipient animal, maintaining the second recipient animal under conditions in which the protooncogene is overexpressed in the animal, recovering a B cell from the second recipient animal, culturing the B cell under conditions in which the protooncogene is overexpressed, and recovering the antibody from the B cell culture.

In some embodiments, the protooncogene is MYC.

In some embodiments, the bone marrow-derived stem cells have been transduced with a nucleic acid molecule encoding an anti-apoptosis protein.

In some embodiments, the anti-apoptosis protein is Bcl-2.

In some embodiments, the nucleic acid molecule is introduced retrovirally.

In some embodiments, the bone marrow-derived stem cells are from a human.

In some embodiments, the bone marrow-derived stem cells are conditionally immortalized long term hematopoietic stem cells.

In some embodiments, the recipient animal is a sublethally irradiated NOD/SCID mouse.

In some embodiments, the animal is transgenic for a nucleic acid molecule encoding the human Ig locus.

DESCRIPTION OF THE INVENTION

The present invention provides novel methods for the production of antibody producing cells and antibodies that overcome many of the problems associated with conventional antibody production. In general, the present invention relates to methods for rapidly producing antibody producing cells and antibodies in protooncogene expressing animals, for example, animals that overexpress MYC or Akt, with MYC being particularly preferred. The methods disclosed herein allow for monoclonal antibody production without the need to fuse antibody producing B cells with a myeloma fusion partner, thereby decreasing the time required to produce the antibody. The methods disclosed herein further obviate the need for B-cells from an immunized mouse to be at a particular stage in the cell cycle in order to successfully fuse with the myeloma partner, as is required in conventional antibody production techniques. The present invention also allows the efficient production of antibodies specific for antigens that are normally subject to immunological constraints such as self tolerance. For example, the methods may be used to produce monoclonal antibodies to self antigens.

Figure 2:
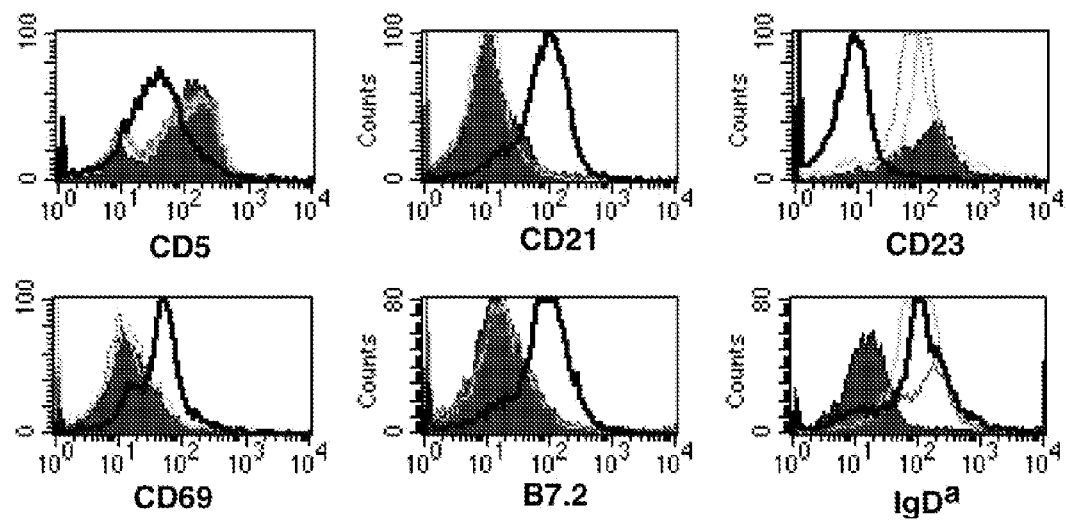
FIG. 2 shows the surface phenotype of tumors and cell lines that arise in Eµ-MYC/BCR$^{HEL}$/sHEL transgenic mice (top panel) and the immunoglobulin production (A) and HEL specific titers (B) in tumors and cell lines that arise in Eµ-MYC/BCR$^{HEL}$/sHEL mice (bottom panel).
Figure 2:
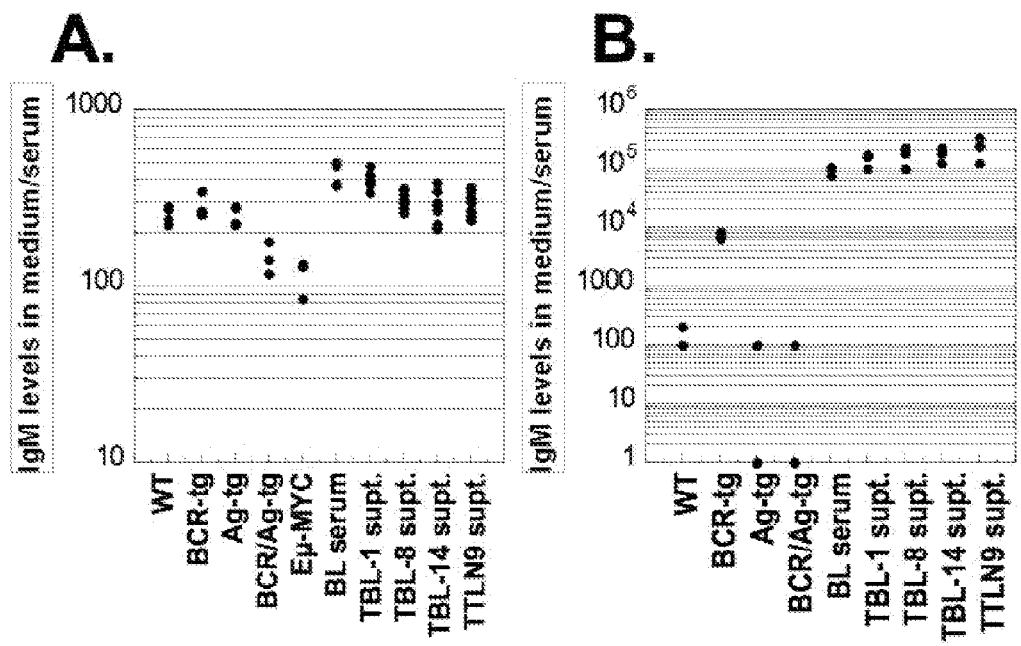

The present inventors have demonstrated that a surfeit of MYC can break B-cell tolerance to a soluble antigen. For example, MYC-overexpressing, BCR$^{HEL}$ transgenic B-cells mount a vigorous response to sHEL and engender a polyclonal autoimmune lymphoprolifeative disease prior to the onset of a malignancy (See FIGS. 3 and 4). The overexpression of MYC in autoreactive B-cells is able to render the B-cells independent of T-cell help, through MYC's abilities to provide proliferative and survival signals. The expanded population of MYC-overexpressing, autoreactive B-cells develop into a B-cell lymphoma that remains dependent upon both continuous exposure to its cognate antigen and overexpression of MYC. B-cells harvested from the lymph nodes, spleens and bone marrow from the tumor-bearing mice can be used to establish many cell lines that express the BCR$^{HEL}$ transgene and secrete anti-HEL IgM, without fusing the primary cells to a myeloma fusion partner (See FIG. 2). This protocol can be readily adapted to virtually any antigen, as discussed below.

Similar results have been obtained using two additional animal protocols. One example is mice derived from a cross between the Ars.A1 mouse and the Eµ-MYC strain. In those mice, the development of a Burkitt's like lymphoma occurs on average at 36 days of age. The tumors are composed of mature, activated B-cells. Those cells express IgM on their surface. Thus, the inventors have demonstrated that MYC overexpression can break tolerance for autoreactive B-cells in the context of a low-affinity, anti-DNA antibody.

The second example utilizes MMTV-rtTA/TRE-MYC mice, which enable the B-cell specific, temporally regulated overexpression of MYC following the withdrawal of doxycycline from the diet. When we withdrew the mice from the doxycycline containing diet at four months of age, the mice accumulated activated peripheral B-cells, anti-nuclear antibodies in their serum, immune complex deposition in their kidneys and developed B-cell lymphomas within 6 weeks (average instance was 42 days). Importantly, we have been able to establish cell lines from the tumors without fusion to a myeloma partner cell.

The present invention provides a novel approach to produce antibodies with a known specificity, with significantly increased potency over current approaches, based on at least three aspects of the biology of the system. First, the absence of the barrier imposed by the mechanisms of self-tolerance enable this system to generate antibodies without any immunological constraints. This approach allows the generation of antibody specificities that cannot be accomplished by standard (state of the art) immunization procedures. In addition, there are no simple means to break self-tolerance with standard immunization protocols. Second, the cognate antigen of interest drives B-cell neoplasia in vivo, and allows for the selection of the antibody producing cells that can develop into lymphoma, and the resulting monoclonal antibody producing cell lines. This accelerates the time for development, since the screening of the resulting monoclonal antibodies can be done in a directed manner. Third, the ability to generate and clonally expand antibody producing cell lines from the tumors that arise in these mice precludes the need to fuse the antibody producing splenic B-cells with a myeloma fusion partner. The conventional fusion process is fairly inefficient and only allows for the immortalization of a fraction of the B-cells that proliferate after immunization, and hence, limits the number of specificities that may be derived in the form of a monoclonal antibody. There are many reasons for this inefficiency (e.g., the need for B-cells to reside in the S phase of the cell cycle, an appropriate number and combination of chromosomes derived from the B-cell and the myeloma fusion partner need to be retained in the cell, the need to survive HAT and 6-TG selection, etc.). In sum, the novel approach of the present invention for generation of monoclonal antibodies provides many more antibodies in a much shorter time frame than traditional approaches. Several variations to the approach exist using tools currently available, selected embodiments of which are summarized below.

In one embodiment of the invention, a suitable non-human animal to be used to produce antibodies includes any non-human animal that is capable of producing antibodies and that overexpresses (e.g., as the result of genetic modification or natural or directed mutation) at least one protooncogene that promotes cell survival and proliferation. Preferred protooncogenes to be overexpressed by the non-human animal used in the method of the invention include, but are not limited to MYC or Akt (myrystylated), with MYC being particularly preferred. By way of example, MYC-overexpressing mice are described in detail herein, but it is to be understood that variants of this protocol, including the use of other suitable protooncogenes and other animals, as well as variations in the technical details of carrying out the protocols, will be contemplated based on this disclosure and are encompassed by the invention.

Any MYC-overexpressing animal may be used with the current invention. Such animals preferably include non-human mammals, and more preferably, a rodent, and even more preferably, a mouse. Particularly useful animals overexpress MYC predominantly in the B cell population, such as, for example, the Eµ-MYC mouse strain. Preferred animals also include those that overexpress MYC in an inducible manner. In these animals, MYC overexpression can be regulated in a temporal manner, e.g., suppressed until the production of the antibodies commences. For example, the MMTV-rtTA/TRE-MYC mouse strain may be administered doxycycline or tetracycline from birth until they are to be used to produce the antibody of interest, thereby minimizing the formation of spontaneous lymphoproliferative diseases. MYC overexpression can be commenced by removing the doxycycline or tetracycline from the diet of the mice. Many additional inducible gene expression/repression systems suitable for use in the present invention are known in the art. Suitable mice may also be generated by retroviral transduction and adoptive transfer techniques. For example, bone marrow cells or purified B-cells from TRE-MYC mice may be retrovirally transduced with rtTA and transferred into recipient mice or cultured in vitro. The resulting cells may also be further transduced (e.g., with an antigen of interest) prior to transfer or culture.

In certain embodiments of the invention, animals possessing MYC-overexpressing cells are introduced to (e.g., exposed to) an antigen in vivo and allowed to mount an immune response to the antigen. For example, in one aspect, the animal may be exposed to the antigen of interest by conventional routes of introduction of an exogenous antigen into an animal that are well known in the art (e.g., using techniques similar to immunization).

Alternatively, and in a preferred embodiment, the animals possessing cells that inducibly express MYC may be engineered to express the antigen of interest by techniques common in the art, or cells expressing the antigen of interest may be introduced into the animal. Examples include retroviral-mediated transduction of bone marrow hematopoietic stem cells, production of transgenic animals (or crossing the MYC-overexpressing animals with an existing transgenic animal that expresses the antigen, or any other method for gene delivery into the animal. In some embodiments, the animals are maintained under conditions in which MYC is not overexpressed until the production of antibodies is desired. The animals may then be maintained under conditions under which MYC is overexpressed to generate B cells that produce antibodies specific for the antigen of interest. The inventors believe that the B cells specific for the antigen will be tolerized to the antigen in the absence of MYC overexpression. Once MYC overexpression is induced, the B cells are able to break tolerance to the neo-self antigen and generate antibodies specific for the antigen.

Cell lines from the normal AN-1 cell population (a population also known as T3 during B-cell development, which are thought to be the B-cells that were anergized in the bone marrow upon binding self-antigen) may be produced by multiple approaches, several of which are described and exemplified below. In one embodiment, the AN-1 population are from MMTV-rtTA/TRE-MYC mice maintained on doxycycline since conception. In accordance with the method of the invention, those mice should also express the specific antigen of interest. As discussed above, this can be readily accomplished through the retroviral-mediated transduction of bone marrow hematopoietic stem cells, standard transgenic approach, or any other method for gene delivery into mice. Cells can be isolated from the spleens of approximately 6 week old mice, as well as either wild type mice, or mice that only carry one of the transgenes. The cells can be plated in vitro in a suitable lymphocyte media (e.g., RPMI 1640, 10% fetal calf serum, pen/strep, L-glutamine, 2-β mercaptoethanol, sodium pyruvate, Hepes and non-essential amino acids) in the presence, or absence of doxycycline (50 nM). The cells are plated at a density of approximately $2 \times 10^6$ cells/ml, in 24 well plates, for example, although these steps can easily be optimized or modified by those of skill in the art. The media is typically replaced once a week. This approach can provide cell lines with an efficiency of 10-70%, depending of the source and status of the cells (i.e. tumorous or normal cells, organ, etc.). The cells may be examined for clonal expansion visually. Any clones that begin to expand at about 14-28 days can be slowly expanded into 6 well plates and eventually into tissues culture flasks. All multiclonal cell lines may be subjected to single cell cloning by limiting dilution approaches prior to analysis, as previously described and known in the art.

In another embodiment, the transformation of B-cell lines capable of producing antibodies of interest may be allowed to occur in vivo. By means of example, cohorts of MMTV-rtTA/TRE-MYC mice (that also express the antigen of interest from a cDNA encoding plasmid) that had been maintained on a doxycycline containing diet since conception, are switched to normal mouse chow at 6 weeks of age. The mice can be examined daily for clinical signs associated with the development of B-cell lymphomas (scruffy fur, externally evident lymphadenopathy, dehydration, sluggishness, hind limb paralysis—ascending, etc). In addition, the mice can be bled periodically and tested for reactivity to the antigen of interest. Once the mice develop tumors, their lymph nodes, spleen, bone marrow, and serum are collected. The resulting cell suspensions may be used for FACS analysis, cells are plated to generate cell lines, as described above, and the remaining cells are frozen in 10% DMSO in order to have continuous access to viable, primary tumor tissue. The serum may be used to stain cells that express the antigen of interest, and for western blot and ELISA assays directed against that specific antigen. Control mice typically include wild type, and singly transgenic, mice.

In another embodiment, purified B-cells from MMTV-rtTA/TRE-MYC mice (that have been maintained on a doxycycline containing diet since conception, as above) can be transduced in vitro so that they express the antigen of choice. The transduced cells can then be adoptively transferred into recipient mice (e.g., wild type mice) that are not maintained on doxycycline, which induces the overexpression of MYC in the transferred B-cells. The mice can then be examined daily for clinical signs associated with the development of B-cell lymphomas, and cell lines generated as described above.

An additional approach for accomplishing the establishment of monoclonal antibody producing cells involves the use of bone-marrow retroviral chimeras from mice that express a selected combination of a protooncogene that promotes cell survival and proliferation (and is preferably regulatable (inducible, controllable)) and a nucleic acid molecule encoding a protein that inhibits apoptosis. In this embodiment, an exemplary combination includes, but is not limited to, MYC-ER and Bcl-2. This latter approach involves the addition of 4-hydroxytamoxyfen (4OHT) in order to render the expressed MYC active. The present inventors have used such a construct successfully to regulate MYC function in the experiments concerned with the conditional immortalization of long-term hematopoietic stem cells. In this instance, a cohort of bone marrow chimeric mice may be generated using 5FU enriched bone marrow derived stem cells, as follows. For bone marrow derived hematopoietic stem cells, 5 mg/mouse of 5-fluorouracil (5FU) is administered intravenously, in order to enrich for long-term HSCs, and to induce their proliferation in vivo. The bone marrow cells are collected from the femurs and tibial bones 5 days later. The red blood cells are lysed, using a hypotonic lysis buffer. The remaining cells are washed twice in media and plated at a concentration of $2\times10^6$ cells/ml, in a 24 well plate, in DMEM media supplemented with 15% heat inactivated fetal calf serum, penicillin/streptomycin, L-glutamine, Non-essential amino acids, recombinant human IL-3, IL-6 and Stem Cell Factor (SCF). As discussed above, the bone marrow cells may be transduced in vitro so that they express the antigen of choice. The cells are cultured for 24 hours prior to the first spin infection, and subjected to the procedure 3 times, every 24 hours. A day after the last spin infection, the cells are analyzed by flow cytometry. As an example, lentivirally transduced bone marrow derived HSCs may be used to reconstitute lethally irradiated mice, and the expression of the reporter gene GFP in lymphoid organs 12 weeks later can be used to track the cells. In this instance, the mice are allowed to reconstitute a normal peripheral lymphoid compartment (8-12 weeks after bone marrow transplantation). The splenic, GFP+ AN-1/T3 cells may then be isolated from those mice and used for in vitro immortalization protocols, as described above. The key difference is that instead of withdrawing doxycycline from the system, 4OHT is added to the medium. Alternatively, those sorted, GFP+AN-1/T3 cells can be adoptively transferred into cohorts of wild type recipient mice that are treated once weekly with 1 mg/mouse of 4OHT, intraperitoneally. The mice are monitored daily for the appearance of clinical signs associated with the development of B-cell lymphomas or leukemia. The resulting tumors can be collected and used for generating B-cell lines as described earlier in this section, using 4OHT instead of doxycycline as the regulator of MYC function.

In another embodiment, conditionally immortalized bone marrow-derived stem cell lines may be used in place of the 5FU enriched bone marrow derived stem cells in the method described above. In some embodiments, a cell line that expresses the above-described combination of a protooncogene that promotes cell survival and proliferation (and is preferably regulatable (inducible, controllable)) and a nucleic acid molecule encoding a protein that inhibits apoptosis, exemplified by the combination of MYC-ER and Bcl-2, may be used. A detailed description and examples of conditionally immortalized bone marrow-derived stem cell lines and their production are described in International Publication No. WO 2007/047583, the contents of which are incorporated herein by reference. WO 2007/047583 provides a detailed description of additional combinations of protooncogene and anti-apoptosis genes and their derivatives that may also be used in the present invention. In certain embodiments, the cell lines may be transduced in vitro so that they express the antigen of choice.

A polyclonal population of antibodies specific for the antigen of interest, as well as the cells producing the antibodies, may be isolated directly from the tissues (spleen, lymph nodes, etc.) or serum of the animal. In another embodiment, monoclonal populations of antibody producing cells may be isolated by standard procedures, and monoclonal antibodies may be recovered from the culture media.

The methods of the present invention may also be used to produce cell lines that produce human antibodies. Two exemplary techniques to achieve this embodiment involve: (1) the crossing (by breeding) of a mouse strain that carries a transgenic BAC construct encoding the human immunoglobulin locus (IgH and IgL) into either: the Eµ-MYC strain or a mouse comprising the MMTV-rtTA/TRE-MYC transgenes, or (2) the use of retroviral bone marrow chimeras that comprise a cDNA for MYC-ER (or another suitable inducible protooncogene). In this latter approach, the cognate antigen of interest is expressed as a neo-self antigen from a retrovirally encoded cDNA, from a traditional transgene, or by other means of gene and protein delivery. The key difference in this embodiment, as compared to those described above, is that the antibodies produced in this setting would be human proteins.

A second way to produce cell lines that produce human antibodies is based on the isolation of peripheral blood B-cells obtained from humans who have a serum antibody titer to a certain protein of interest. The B-cells are purified using standard approaches. The purified B-cells can be panned on plastic plates coated with the protein of interest in order to enrich for those B-cells with a specificity of interest. Alternatively, the protein of interest can be conjugated to magnetic beads that can then be used to isolate the B-cells with the specificity of interest. Those cells can then be single-cell sorted into Terasaki plates for single cell RT-PCR. cDNAs are generated for the VDJ joint region for the IgH and IgL genes for each of the B-cells isolated. Those cDNA fragments can then be cloned into retroviral vectors that encode a human IgH and/or IgL and contain a multiple cloning site in the location where those molecules would normally have their own VDJ sequence (either one of IgH and one for IgL, or a retroviral vector that encodes LTR-IgH-IRES-IgL-LTR). The resulting retroviruses can be sequenced and used to transduce 5FU enriched bone marrow derived HSCs derived from a mouse that overexpresses MYC and contains a genetic modification that prevents the production of B-cells. Examples include MMTV-rtTA/TRE-MYC/Rag-1$^{-/-}$ mice, Eµ-MYC/Rag-1$^{-/-}$ mice, or Rag-1$^{-/-}$ bone marrow co-infected with the IgH/IgL retrovirus and one for MYC-ER. Additional examples include any of the MYC-overexpressing mice described above crossed with a mouse containing a genetic ablation of a locus, such as Rag-2$^{-/-}$, SCID, DNA-PK$^{-/-}$, Ku70$^{-/-}$, Ku80$^{-/-}$, XRCC4$^{-/-}$, µMT$^{-/-}$, etc. Those cells can then be used to reconstitute lethally irradiated mice using the protocol described earlier (for retroviral bone marrow chimeric mice). Any means to transduce nucleic acids encoding the specific antigen into mice (gene gun, naked DNA immunization, transgenic mice, lentiviral "transgenic" mice, direct injections with recombinant protein, vaccinia viruses that encode the cDNA for the gene, recombinant adenoviruses, recombinant yeast, or mammalian cells, tat-fusion proteins, etc.) can be used. The resulting cell lines obtained from this approach will encode human immunoglobulin sequences specific for the protein of interest. This is a powerful novel approach for the generation of cocktails of inhibitory antibodies against a variety of pathogens and diseases, including viral infections, tumors, bacteria and fungi, etc.

Figure 9:
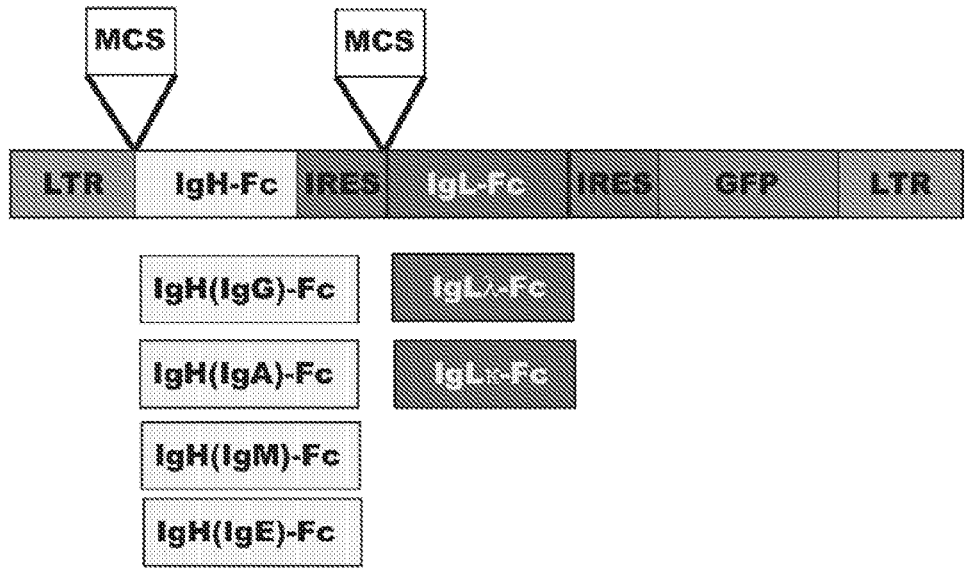
FIG. 9 shows two retroviral vector-based approaches to humanize the antibody specificities obtained through the use of the MYC-overexpressing mice.
Figure 9:
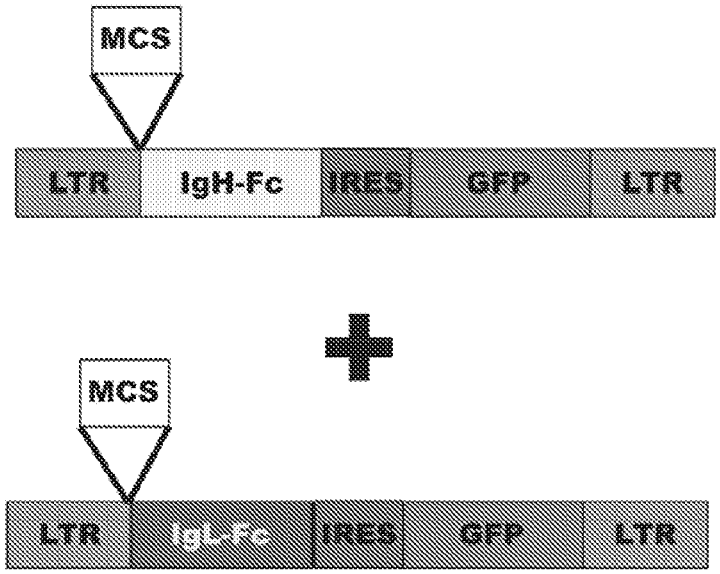

The present invention also includes methods to humanize the antibody specificities obtained through the use of the MMTV-tTA/TRE-MYC mice. In this case, the rearranged VDJ joint sequence derived from the murine IgH and VJ regions in the IgL loci are PCR amplified. Those sequences can be obtained from clonal cell lines that develop from the MMTV-tTA/TRE-MYC mice and have been already shown to produce antibodies to the antigen of interest. The PCR-amplified fragments can be cloned into a retroviral plasmid that encodes a human IgH and IgL sequences that contain a multiple cloning site into which the PCR fragments are cloned (See FIG. 9). The IgH and IgL sequences are spaced by an IRES element, such that both cDNAs are expressed from the same viral vector. Use of different viral vectors enables the generation of different antibody isotypes, with the given specificities (IgA, IgG, IgM, IgE and different subgroups thereof). In addition, the sequences encoding the Fc regions may be further modified to minimize the ability of the resulting antibodies to trigger autoimmune reactions and related immune-complex deposition problems. The resulting retroviruses are used to transduce bone marrow derived hematopoietic stem cells obtained from Rag-1$^{-/-}$/MMTV-tTA/TRE-MYC mice. The transduced cells can be transplanted into cohorts of lethally irradiated C57/BL6 wild type mice. The resulting mice are monospecific to one antigen, and can generate monoclonal antibody producing cells with all of the added features of the humanized antibodies.

In another embodiment, monoclonal human antibodies to an antigen of interest can be produced by the following method. Instead of amplifying a specific VDJ joint sequence from IgH and IgL found in a given cell line, PCR-amplified fragments for rearranged VDJ from IgH and IgL sequences found in B-cells obtained from either healthy donors, patients who suffer from antibody-mediated autoimmune dieases (e.g., Sjögren's syndrome, Hashimoto's thyoditis, Systemic Lupus Erythematosus, Waldenström's macroglobulinemia, etc), as well as patients who suffer from Non-Hodgkin's lymphomas (Burkitt's lymphoma, Follicular Like Lymphomas, Diffuse Large B-cell lymphomas, MGUS and Multiple Myeloma) can be isolated. The PCR fragments are cloned into the retroviral constructs described above (which can also be prepared as two different retroviral constructs to expedite the generation of these libraries). The retroviral libraries can then be used to transduce bone marrow derived hematopoietic stem cells (HSCs) obtained from Rag-1$^{-/-}$/MMTV-tTA/TRE-MYC mice in order to generate bone marrow chimeric mice, as described above. The bone marrow chimeric mice only make B-cells that express human immunoglobulins, and can be maintained on a doxycycline containing diet until they are ready for immunization (in order to suppress MYC overexpression). These mice can be immunized in the absence of doxycycline (in order to attain MYC overexpression in their B-cells). The reactive, antigen-specific B-cells can be isolated and enriched in vitro by panning against the specific antigen. The cells can be grown in the presence of MYC overexpression in order to immortalize them and make a monoclonal cell line that makes human antibodies.

As described above, this approach can be used to specifically isolate human antibodies having different isotypes, including, for example, human IgA antibodies to specific antigens. IgA antibodies are highly sought after for prophylaxis, it remains unclear how to immunize animals using conventional antibody production methods in order to deliberately induce IgA production. Using the present invention, this problem is resolved. Moreover, any one specificity defined here can be easily transferred to another Fc backbone as described above.

It is possible that the resulting cell lines may not optimally produce large amounts of antibody. This can be overcome by the PCR-based amplification of the cDNAs that encode for IgH and IgL. Cloning of those cDNAs into expression vectors can then be used to transduce myeloma cell lines (or other B-cell lymphoma cell lines) to increase antibody production.

The third approach is to retrovirally transduce human ctlt-HSC cell lines with the antigen of interest and use those transduced ctlt-HSC cell lines to transplant sublethally irradiated NOD/SCID mice. The mice can be given injections of 4OHT and the resulting leukemia/lymphomas can be cultured to produce the human monoclonal antibody producing cell lines. The advantage is that the entire monoclonal antibody can be encoded by human genes and mature in vivo.

A fourth possibility is to isolate splenic mature human B-cells derived from NOD/SCID mice that were sublethally irradiated and reconstituted with human ctlt-HSC cell lines. The mature B-cells that developed in the absence of MYC overexpression can be retrovirally transduced with the antigen of interest. The cells can either be transplanted back into sublethally irradiated NOD/SCID mice and transformed in vivo by injecting those mice with 4OHT, or maintained in vitro culture in the presence of 4OHT. This may allow for the development of novel human monoclonal antibodies in 2-3 weeks starting with only the nucleic acid sequence of the antigen of interest.

The ability of MYC to break B-cell tolerance to self-antigens may also result in the development of antibodies to a number of specificities, regardless of the T-cell immunodominant epitope. The mechanism whereby MYC breaks B-cell tolerance involves rendering the autoreactive B-cells independent of T-cell help, and can thus also free them from the constrains of responding to specific portions of a protein sequence. This approach may be able to unveil virally encoded epitopes that mimic self-proteins and are normally ignored by the immune system, and therefore, tolerance mechanisms typically prevent good responses to those residues. The present invention thus provides a novel method to render those common domains good vaccine candidates.

The technologies disclosed herein provide new strategies for the rapid development of diagnostic and therapeutic antibodies for the detection and treatment of emerging infectious diseases and chronic illnesses such as cancer and autoimmunity. Because of the speed and efficiency of the present invention in comparison to existing procedures for antibody production, these antibodies can be generated soon after a new infectious agent arises. For example, antibodies specific for viruses responsible for a sudden outbreak of disease (e.g., pandemic flu) may be ready for use as therapeutics in a much shorter period than those generated by current methods. The antibodies produced using the methods of the present invention may comprise antibodies of all types and classes, as well as antibody-binding fragments and derivatives of antibodies. More particularly, antibodies produced by the methods of the present invention can include serum containing such antibodies, or antibodies that have been purified to varying degrees. Whole antibodies of the present invention can be polyclonal or monoclonal. Alternatively, functional equivalents of whole antibodies, such as antigen binding fragments in which one or more antibody domains are truncated or absent (e.g., Fv, Fab, Fab', or F(ab)$_2$ fragments), as well as genetically-engineered antibodies or antigen binding fragments thereof, including single chain antibodies, human antibodies, humanized antibodies (discussed above), antibodies that can bind to more than one epitope (e.g., bi-specific antibodies), or antibodies that can bind to one or more different antigens (e.g., bi- or multi-specific antibodies), may also be produced by the methods of the invention.

Antibodies capable of selectively binding to a wide range of antigens can be produced by the methods of the present invention. In general, any antigen capable of inducing an immune response when introduced to an animal is suitable for use in the present invention. In addition, antigens that would normally be subject to self tolerance mechanisms in normal animals, such as auto antigens, may also be used in the present invention. For example, the antigens can include, but are not limited to, any antigens associated with a pathogen, including viral antigens, fungal antigens, bacterial antigens, helminth antigens, parasitic antigens, ectoparasite antigens, protozoan antigens, or antigens from any other infectious agent. Antigens can also include any antigens associated with a particular disease or condition, whether from pathogenic or cellular sources, including, but not limited to, cancer (tumor) antigens, antigens associated with an autoimmune disease (e.g., diabetes antigens), allergy antigens (allergens), mammalian cell molecules harboring one or more mutated amino acids, proteins normally expressed pre- or neo-natally by mammalian cells, proteins whose expression is induced by insertion of an epidemiologic agent (e.g. virus), proteins whose expression is induced by gene translocation, and proteins whose expression is induced by mutation of regulatory sequences. These antigens can be native antigens or genetically engineered antigens which have been modified in some manner (e.g., sequence change or generation of a fusion protein).

In one aspect, the antigen is from virus, including, but not limited to, adenoviruses, arena viruses, bunyaviruses, coronaviruses, coxsackie viruses, cytomegaloviruses, Epstein-Barr viruses, flaviviruses, hepadnaviruses, hepatitis viruses, herpes viruses, influenza viruses, lentiviruses, measles viruses, mumps viruses, myxoviruses, oncogenic viruses, orthomyxoviruses, papilloma viruses, papovaviruses, parainfluenza viruses, paramyxoviruses, parvoviruses, picornaviruses, pox viruses, rabies viruses, respiratory syncytial viruses, reoviruses, rhabdoviruses, rubella viruses, togaviruses, and varicella viruses. Other viruses include T-lymphotrophic viruses, such as human T-cell lymphotrophic viruses (HTLVs, such as HTLV-I and HTLV-II), bovine leukemia viruses (BLVS) and feline leukemia viruses (FLVs). The lentiviruses would include, but are not limited to, human (HIV, including HIV-1 or HIV-2), simian (SIV), feline (FIV) and canine (CIV) immunodeficiency viruses.

The generation of monoclonal antibodies with the novel procedures of the invention can lead to the development of novel specificities that could potentially neutralize entire clades of HIV variants. This could be attained, for example, either by targeting an obligatory structural component of the viral envelope proteins, or alternatively, a host coreceptor protein.

In one preferred embodiment, methods of the present invention may also be used to generate antibodies specific for influenza virus proteins, such as the hemagglutinin (HA) protein or neuraminidase (NA) protein. In some embodiments the HA protein is selected from: H1, H2, H3, H4, H5, H6, H7, H8, H9, H10, H11, H12, H13, H14, H15 and H16. In one aspect, the HA protein is H5. In one aspect, the NA protein is selected from: N1, N2, N3, N4, N5, N6, N7, N8 and N9. In one aspect, the NA protein is N5. In certain embodiments, the antibody is specific for a subunit of an HA protein.

In another aspect, the antigen is from an infectious agent from a genus selected from: *Aspergillus, Bordatella, Brugia, Candida, Chlamydia, Coccidia, Cryptococcus, Dirofilaria, Escherichia, Francisella, Gonococcus, Histoplasma, Leishmania, Mycobacterium, Mycoplasma, Paramecium, Pertussis, Plasmodium, Pneumococcus, Pneumocystis, Rickettsia, Salmonella, Shigella, Staphylococcus, Streptococcus, Toxoplasma, Vibriocholerae Yersinia*. In one aspect, the infectious agent is selected from *Plasmodium falciparum* or *Plasmodium vivax*.

In one aspect, the antigen is from a bacterium from a family selected from: Enterobacteriaceae, Micrococcaceae, Vibrionaceae, Pasteurellaceae, Mycoplasmataceae, and Rickettsiaceae. In one aspect, the bacterium is of a genus selected from: *Pseudomonas, Bordetella, Mycobacterium, Vibrio, Bacillus, Salmonella, Francisella, Staphylococcus, Streptococcus, Escherichia, Enterococcus, Pasteurella*, and *Yersinia*. In one aspect, the bacterium is from a species selected from: *Pseudomonas aeruginosa, Pseudomonas mallei, Pseudomonas pseudomallei, Bordetella pertussis, Mycobacterium tuberculosis, Mycobacterium leprae, Francisella tularensis, Vibrio cholerae, Bacillus anthracis, Salmonella enteric, Yersinia pestis, Escherichia coli* and *Bordetella bronchiseptica*.

Suitable antigens also include the cellular receptors to which viruses bind (e.g., CD4, etc.).

According to the present invention, the phrase "selectively binds to" refers to the ability of an antibody or antigen-binding fragment thereof to preferentially bind to specified proteins or other antigens. More specifically, the phrase "selectively binds" refers to the specific binding of one protein to another (e.g., an antibody or antigen-binding fragment thereof to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen-binding fragment thereof in the absence of the antigen is considered to be background. Binding can be measured using a variety of methods standard in the art including enzyme immunoassays (e.g., ELISA), immunoblot assays, etc.).

According to the present invention, antigens suitable for use in the present invention can include two or more immunogenic domains or epitopes from the same antigen; two or more antigens, immunogenic domains, or epitopes from the same cell, tissue or organism; and/or two or more different antigens, immunogenic domains, or epitopes from different cells, tissues or organisms. Indeed, the present invention provides methods for generating monoclonal antibodies of multiple specificities after one immunization. For example, the mice described herein (e.g., MMTV-tTA/TRE-MYC mice) may be immunized with two or more immunogenic domains, epitopes, or other antigens, such as antigens generated as recombinant proteins in bacteria or yeast, and made as GST-fusion proteins, using standard immunization techniques. The B-cells from the immunized mice may then be isolated by, for example, panning on plates coated with the purified protein antigens. The isolated, antigen-specific B-cells may be cultured in the absence of antibiotic (e.g., doxycycline) in order to activate MYC overexpression and transform the B-cells in vitro in the presence of continuous antigen. The resulting cell lines may then be screened for antibody production and specificity. This approach may allow the rapid production of monoclonal antibodies specific for as many as 200 antigens at once, and may resolve a major bottleneck in the field of proteomics by providing a plentiful supply of monoclonal antibodies to many proteins.

The methods described above may be used to generate neutralizing antibody compositions that recognize many or all epitopes of an antigen or multiple antigens. For example, mice may be immunized with several antigens of one virus or with multiple variants of a particular antigen from several related viral strains. The isolated, antigen-specific B-cells may then be panned for cells that produce antibodies specific for particular epitopes of an antigen. These may then be combined to produce an antibody composition that binds to most or all epitopes of a virus or all variants of a specific antigen from a panel of viral strains. Similarly, the antibodies may be selected by similar methods for binding to one particular antigen or epitope, without cross reactivity to similar epitopes.

Antibodies useful as prophylactic or therapeutic agents produced by the present invention are typically provided in the form of a composition (formulation). In one embodiment of the invention, a pharmaceutical composition or formulation is prepared from an effective amount of an antibody or antigen-binding fragment thereof and a pharmaceutically acceptable carrier. Pharmaceutically acceptable carriers are well known to those with skill in the art. According to the present invention, a "pharmaceutically acceptable carrier" includes pharmaceutically acceptable excipients and/or pharmaceutically acceptable delivery vehicles, which are suitable for use in the administration of a formulation or composition to a suitable in vivo site. Pharmaceutically acceptable carriers may be capable of maintaining an antibody used in a formulation in a form that, upon arrival of the antibody at the target site in a patient, the antibody is capable of acting, preferably resulting in a therapeutic benefit to the patient.

Accordingly, the present invention also includes methods of treating an individual using one or more of the antibodies or derivatives thereof produced by the invention. The invention includes, in one embodiment, a method to treat an animal that has or is at risk of developing a condition or disease (including prevention and/or therapeutic treatment of the condition or disease), including an infection by a pathogen (e.g., a coronavirus infection) or a disease resulting therefrom. The method includes the step of administering to an animal that has or is at risk of developing the disease or condition one or more antibodies or functional derivatives thereof that are produced by the present invention as described herein, to reduce or prevent the disease or condition, including prevention or reduction in at least one symptom resulting from the disease or condition in the animal.

Although the present invention has been exemplified using mice, it will be appreciated by one of skill in the art that any experimental animal known in the art for use in antibody production may be used. The methods of the present invention can be used in any organism suitable for antibody production, including a cell or tissue thereof. Preferred animals include any animal of the Vertebrate class, Mammalia (i.e., mammals), including, without limitation, primates, rodents, livestock and domestic pets. Generally, in the production of an antibody, a suitable experimental animal, such as, for example, but not limited to, a rabbit, a sheep, a hamster, a guinea pig, a mouse, a rat, or a chicken, is exposed to an antigen against which an antibody is desired. In a preferred embodiment, the animal is a "humanized" animal, for example, a NOD/SCID mouse reconstituted with human ctlt-HSC cell lines that yield human antibodies and human monoclonal producing cell lines.

General Definitions

The practice of the present invention may employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994); Harlow and Lane (1988) *Antibodies, A Laboratory Manual*, Cold Spring Harbor Publications, New York; Harlow and Lane (1999) *Using Antibodies: A Laboratory Manual* Cold Spring Harbor Laboratory Press, Cold Spring Harbor, N.Y. (jointly referred to herein as "Harlow and Lane"), Beaucage et al. eds., *Current Protocols in Nucleic Acid Chemistry* John Wiley & Sons, Inc., New York, 2000); and *Vaccines*, S. Plotkin and W. Orenstein, eds., $3^{rd}$ edition (1999).

According to the present invention, the general use herein of the term "antigen" refers: to any portion of a protein (peptide, partial protein, full-length protein), wherein the protein is naturally occurring or synthetically derived, to a cellular composition (whole cell, cell lysate or disrupted cells), to an organism (whole organism, lysate or disrupted cells) or to a carbohydrate (such as those expressed on cancer cells), or other molecule, or a portion thereof. An antigen elicits an antigen-specific immune response (e.g., a humoral and/or a cell-mediated immune response) against the same or similar antigens that are encountered within the cells and tissues of an individual to which the antigen is administered. Alternatively, an antigen can act as a toleragen. When referring to stimulation of an immune response, the term "antigen" can be used interchangeably with the term "immunogen". An antigen can be as small as a single epitope, or larger, and can include multiple epitopes. As such, the size of an antigen can be as small as about 5-12 amino acids (e.g., a peptide) and as large as: a full length protein, including a multimer and fusion proteins, chimeric proteins, whole cells, whole microorganisms, or portions thereof (e.g., lysates of whole cells or extracts of microorganisms). In addition, antigens can include carbohydrates.

An "immunogenic domain" of a given antigen can be any portion, fragment or epitope of an antigen (e.g., a peptide fragment or subunit or an antibody epitope or other conformational epitope) that contains at least one epitope that acts as an immunogen when administered to an animal. For example, a single protein can contain multiple different immunogenic domains. Immunogenic domains need not be linear sequences within a protein, such as in the case of a humoral immune response.

An epitope is defined herein as a single immunogenic site within a given antigen that is sufficient to elicit an immune response, or a single toleragenic site within a given antigen that is sufficient to suppress, delete or render inactive an immune response. Those of skill in the art will recognize that T cell epitopes are different in size and composition from B cell epitopes, and that epitopes presented through the Class I MHC pathway differ from epitopes presented through the Class II MHC pathway. Epitopes can be linear sequence or conformational epitopes (conserved binding regions).

"Vaccination" or "immunization" refers to the elicitation (induction) of an immune response against an antigen or portion thereof, as a result of administration of the antigen, alone or together with an adjuvant. The concept of immunization is well known in the art. The immune response that is elicited by administration of an antigen can be any detectable change in any facet of the immune response (e.g., cell-mediated response, humoral response, cytokine production), as compared to in the absence of the administration of the antigen.

According to the present invention, antibodies are characterized in that they comprise immunoglobulin domains and as such, they are members of the immunoglobulin superfamily of proteins. Generally speaking, an antibody molecule comprises two types of chains. One type of chain is referred to as the heavy or H chain and the other is referred to as the light or L chain. The two chains are present in an equimolar ratio, with each antibody molecule typically having two H chains and two L chains. The two H chains are linked together by disulfide bonds and each H chain is linked to a L chain by a disulfide bond. There are only two types of L chains referred to as lambda (λ) and kappa (κ) chains. In contrast, there are five major H chain classes referred to as isotypes. The five classes include immunoglobulin M (IgM or μ), immunoglobulin D (IgD or δ), immunoglobulin G (IgG or λ), immunoglobulin A (IgA or α), and immunoglobulin E (IgE or ε). The distinctive characteristics between such isotypes are defined by the constant domain of the immunoglobulin and are discussed in detail below. Human immunoglobulin molecules comprise nine isotypes, IgM, IgD, IgE, four subclasses of IgG including IgG1 (γ1), IgG2 (γ2), IgG3 (γ3) and IgG4 (γ4), and two subclasses of IgA including IgA1 (α1) and IgA2 (α2). In humans, IgG subclass 3 and IgM are the most potent complement activators (classical complement system), while IgG subclass 1 and to an even lesser extent, 2, are moderate to low activators of the classical complement system. IgG4 subclass does not activate the complement system (classical or alternative). The only human immunoglobulin isotype known to activate the alternative complement system is IgA. In mice, the IgG subclasses are IgG1, IgG2a, IgG2b and IgG3. Murine IgG1 does not activate complement, while IgG2a, IgG2b and IgG3 are complement activators.

Each H or L chain of an immunoglobulin molecule comprises two regions referred to as L chain variable domains ($V_L$ domains) and L chain constant domains ($C_L$ domains), and H chain variable domains ($V_H$ domains) and H chain constant domains ($C_H$ domains). A complete $C_H$ domain comprises three sub-domains (CH1, CH2, CH3) and a hinge region. Together, one H chain and one L chain can form an arm of an immunoglobulin molecule having an immunoglobulin variable region. A complete immunoglobulin molecule comprises two associated (e.g., di-sulfide linked) arms. Thus, each arm of a whole immunoglobulin comprises a $V_{H+L}$ region, and a $C_{H+L}$ region. As used herein, the term "variable region" or "V region" refers to a $V_{H+L}$ region (also known as an Fv fragment), a $V_L$ region or a $V_H$ region. Also as used herein, the term "constant region" or "C region" refers to a $C_{H+L}$ region, a $C_L$ region or a $C_H$ region.

Limited digestion of an immunoglobulin with a protease may produce two fragments. An antigen binding fragment is referred to as an Fab, an Fab', or an F(ab')$_2$ fragment. A fragment lacking the ability to bind to antigen is referred to as an Fc fragment. An Fab fragment comprises one arm of an immunoglobulin molecule containing a L chain ($V_L$+$C_L$ domains) paired with the $V_H$ region and a portion of the $C_H$ region (CH1 domain). An Fab' fragment corresponds to an Fab fragment with part of the hinge region attached to the CH1 domain. An F(ab')$_2$ fragment corresponds to two Fab' fragments that are normally covalently linked to each other through a di-sulfide bond, typically in the hinge regions.

The $C_H$ domain defines the isotype of an immunoglobulin and confers different functional characteristics depending upon the isotype. For example, μ constant regions enable the formation of pentameric aggregates of IgM molecules and α constant regions enable the formation of dimers.

The antigen specificity of an immunoglobulin molecule is conferred by the amino acid sequence of a variable, or V, region. As such, V regions of different immunoglobulin molecules can vary significantly depending upon their antigen specificity. Certain portions of a V region are more conserved than others and are referred to as framework regions (FW regions). In contrast, certain portions of a V region are highly variable and are designated hypervariable regions. When the $V_L$ and $V_H$ domains pair in an immunoglobulin molecule, the hypervariable regions from each domain associate and create hypervariable loops that form the antigen binding sites. Thus, the hypervariable loops determine the specificity of an immunoglobulin and are termed complementarity-determining regions (CDRs) because their surfaces are complementary to antigens.

Further variability of V regions is conferred by combinatorial variability of gene segments that encode an immunoglobulin V region. Immunoglobulin genes comprise multiple germline gene segments that somatically rearrange to form a rearranged immunoglobulin gene that encodes an immunoglobulin molecule. $V_L$ regions are encoded by a L chain V gene segment and J gene segment (joining segment). $V_H$ regions are encoded by a H chain V gene segment, D gene segment (diversity segment) and J gene segment (joining segment).

Both a L chain and H chain V gene segment contain three regions of substantial amino acid sequence variability. Such regions are referred to as L chain CDR1, CDR2 and CDR3, and H chain CDR1, CDR2 and CDR3, respectively. The length of an L chain CDR1 can vary substantially between different $V_L$ regions. For example, the length of CDR1 can vary from about 7 amino acids to about 17 amino acids. In contrast, the lengths of L chain CDR2 and CDR3 typically do not vary between different $V_L$ regions. The length of a H chain CDR3 can vary substantially between different $V_H$ regions. For example, the length of CDR3 can vary from about 1 amino acid to about 20 amino acids. Each H and L chain CDR region is flanked by FW regions.

Other functional aspects of an immunoglobulin molecule include the valency of an immunoglobulin molecule, the affinity of an immunoglobulin molecule, and the avidity of an immunoglobulin molecule. As used herein, affinity refers to the strength with which an immunoglobulin molecule binds to an antigen at a single site on an immunoglobulin molecule (i.e., a monovalent Fab fragment binding to a monovalent antigen). Affinity differs from avidity which refers to the sum total of the strength with which an immunoglobulin binds to an antigen. Immunoglobulin binding affinity can be measured using techniques standard in the art, such as competitive binding techniques, equilibrium dialysis or BIAcore methods. As used herein, valency refers to the number of different antigen binding sites per immunoglobulin molecule (i.e., the number of antigen binding sites per antibody molecule of antigen binding fragment). For example, a monovalent immunoglobulin molecule can only bind to one antigen at one time, whereas a bivalent immunoglobulin molecule can bind to two or more antigens at one time, and so forth.

An "individual" is a vertebrate, preferably a mammal, more preferably a human. Mammals include, but are not limited to, farm animals, sport animals, pets, primates, mice and rats. The term "individual" can be used interchangeably with the term "animal", "subject" or "patient".

Various aspects of the present invention are described in the following experiments. These experimental results are for illustrative purposes only and are not intended to limit the scope of the present invention.

EXAMPLES

Example 1

The following example demonstrates the production of B-cell lines derived from MMTV-tTA/TRE-MYC mice.

In order to generate B-cell lines from AN1/T3 populations of mice that can inducibly overexpress MYC in a B-cell specific manner, we maintained MMTV-tTA/TRE-MYC mice on doxycycline for eight weeks after birth, then switched them to a normal diet. The mice developed an externally evident lymphadenopathy and splenomegaly, and presented with a number of the clinical signs that we have consistently seen associated with lymphoid neoplasia (scruffy fur, hunched posture, labored breathing, anemia, organomegaly, etc.). The mice were euthanized and their lymph nodes and spleens were collected for analysis. We generated single cell suspensions from some of the lymph nodes and a portion of the spleen. Those cells were used for flow cytometric analyses. The initial characterization of the tumors demonstrated the high prevalence of activated B-cells. We used some of the same cells to seed cultures to generate B-cell lines. These cells were cultured in lymphocyte media (RPMI 1640, 10% Fetal Calf Serum, penicillin/streptomycin, L-glutamine, HEPES, non-essential amino acids, sodium pyruvate and 2-β-mercaptoethanol). Approximately 14-21 days later, some of the wells began to exhibit clonal outgrowth of cell lines. The cells were carefully expanded until they adapted to growth in large flasks and a portion of the cells were cryopreserved.

Figure 1:
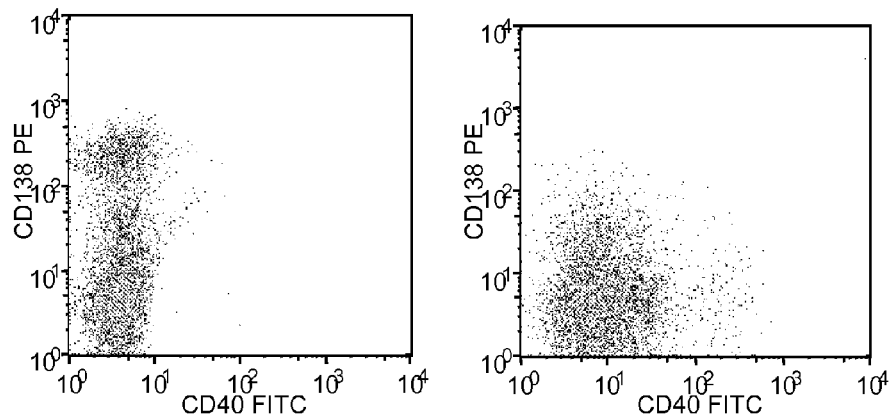
FIG. 1 shows the expression of CD138 (Y-axis) and CD40 (X-axis) on the surface of TBLK6 and TBLK7 cell lines (top panel) and an analysis of IgM secretion from TBLK6 and TBLK7 cell lines (bottom panel).
Figure 1:
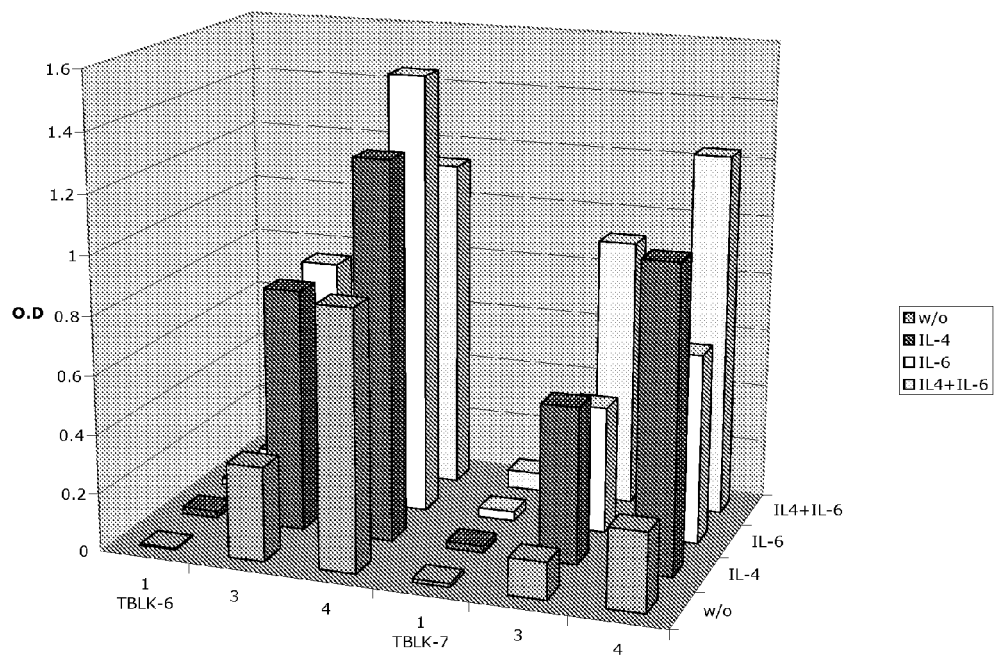

We initially picked two cell lines, designated TBLK6 and TBLK7. Samples of both cell lines were stained with antibodies specific for CD138 (Y-axis) and CD40 (X-axis) and analyzed by flow cytometry. As shown in FIG. 1 (top panel), the two cell lines show different levels of CD138 expression, and little to no CD40 expression. We also measured the levels of immunoglobulin secretion into the tissue culture medium after seeding. A defined number of cells derived from each cell line ($10^5$ cells) were seeded in a well of a 24 well plate, in 1 ml of growth medium alone, or supplemented with either IL-4, IL-6, or both. Samples of the supernatant were collected at 1, 3 or 4 days after the culture was initiated. The supernatants were then used for an anti-IgM capture ELISA. The results presented in FIG. 1 (bottom panel) show that while both cell lines spontaneously secrete immunoglobulin into their growth medium, the levels of secretion can be increased by the addition of IL-4 and IL-6 into the initial inoculum. We then demonstrated that the immunoglobulins secreted by both TBLK6 and TBLK7 are IgM. One can single cell clone both of those cell lines in order to continue to generate true monoclonal populations. In addition, we have now generated a cohort of MMTV-tTA/TRE-MYC bigenic mice that can be used for isolating the AN1/T3 population by cell sorting.

Example 2

The following example demonstrates the surface phenotype and HEL-specific antibody production of tumors and cell lines that arise in Eµ-MYC/BCR$^{HEL}$/sHEL transgenic mice.

Cells obtained from wild type mice (solid histograms), BCR$^{HEL}$ transgenic mice (solid, light gray line), BCR$^{HEL}$/sHEL mice (dotted gray line), and Eµ-MYC/BCR$^{HEL}$/sHEL triply transgenic mice (solid black line) were stained with antibodies specific for the indicated surface markers and analyzed by flow cytometry. The data shown in FIG. 2 (top panel) represent the expression of the indicated markers on B220+ splenocytes.

$10^5$ cells of the cell lines TBL-1, TBL-8, TBL-14 and TTLN9 (all derived from the tumors that arose in Eµ-MYC/BCR$^{HEL}$/sHEL mice) were seeded in a 24 well plate, in 1 ml of growth medium, without any added cytokines. Samples of the supernatants were collected four days later and assayed for the concentration of total IgM (A), as well as for the titer of HEL specific IgM (B). Sera from various control mice are also included to provide a measure to compare antibody production in the cell lines. These mice included wild type C57/BL6 mice (WT), BCR$^{HEL}$ transgenic mice (BCR-tg), sHEL transgenic mice (Ag-tg), BCR$^{HEL}$/sHEL doubly transgenic mice (BCR/Ag-tg), Eµ-MYC mice and tumor-bearing Eµ-MYC/BCR$^{HEL}$/sHEL triply transgenic mice (BL). The results presented in FIG. 2 (bottom panel) demonstrate HEL-specific titers in tumors and cell lines that arise in Eµ-MYC/BCR$^{HEL}$/sHEL mice.

Example 3

The following example demonstrates that MYC can break B-cell tolerance and give rise to antigen driven, MYC-dependent B-cell lymphomas.

By breaking tolerance, MYC may expose B and T cells to sustained stimulation by autoantigens, providing a force that can foster cellular proliferation and the genomic hazards that ensue. Studies of the preneoplastic state of MYC-overexpressing B cells led us to uncover a novel role for MYC in the regulation of B cell tolerance.

Figure 3:
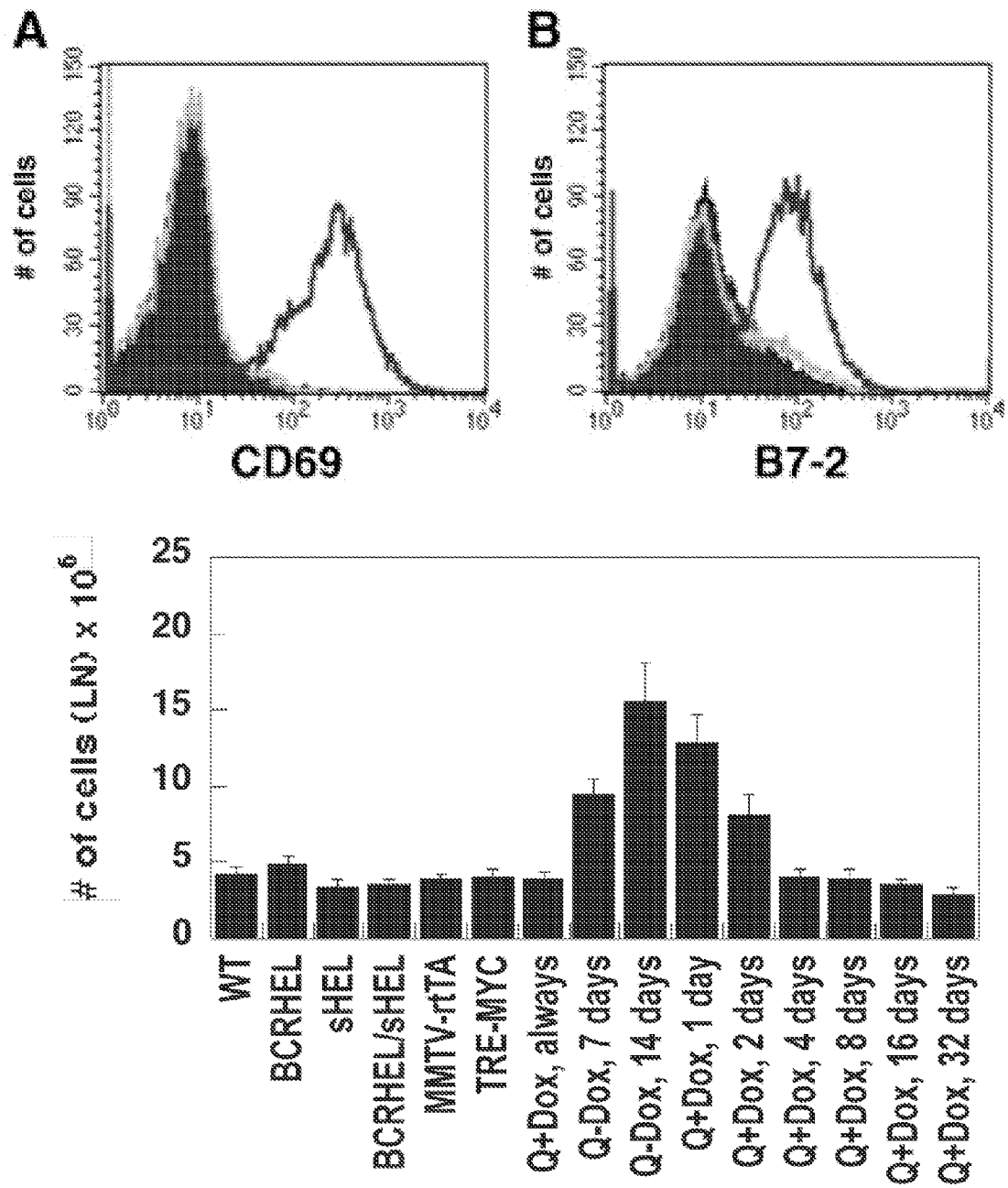
FIG. 3 shows the appearance of activated B-cells following acute overexpression of MYC (top panel) and the accumulation of activated B-cells during the continuous overexpression of MYC (bottom panel).

Flow cytometric analyses were performed on lymph node cells obtained from a wild type mouse (solid histogram), a MMTV-rtTA/TRE-MYC/BCR$^{HEL}$/sHEL mouse that had been kept on doxycycline throughout (light gray line), and an MMTV-rtTA/TRE-MYC/BCR$^{HEL}$/sHEL mouse that had been taken off doxycycline a week prior to euthanasia (dark gray line). FIG. 3 (top panel) shows the results when the cells were stained with antibodies to two molecules that are upregulated following the antigen-dependent activation of B-cells, CD69 (A), and B7-2 (CD86) (B). The indicated levels of CD69 and B7-2 were present on the B220+ fraction of the cells, ascertained by gating on the Cychrome-C staining cells by flow cytometry. The results indicate that activated B cells appear following the acute overexpression of MYC.

FIG. 3 (bottom panel) shows that the accumulation of activated B-cells requires the continuous overexpression of MYC. Each data point in the graphs represents the number of activated B-cells detected in the lymph nodes of an individual mouse. Cohorts of four mice were used for each time point. This figure shows the requirement for MYC in the initiation and maintenance of the accumulation of activated B-cells in induced MMTV-rtTA/TRE-MYC/BCR$^{HEL}$/sHEL mice.

Sera were obtained from wild type mice (1), BCR$^{HEL}$ mice (2), BCR$^{HEL}$/sHEL mice (3), Eµ-MYC/BCR$^{HEL}$/sHEL mice prior to the development of overt tumors (4), MMTV-rtTA/TRE-MYC/BCR$^{HEL}$/sHEL mice that had been maintained on doxycycline throughout (5), and MMTV-rtTA/TRE-MYC/BCR$^{HEL}$/sHEL mice that had been taken off doxycycline 28 days prior to collection of sera (6) and assayed in triplicate by ELISA against HEL (A), or for total serum immunoglobulin (B). The results presented in FIG. 4 (top panel) show the accumulation of autoantibodies in serum following the overexpression of MYC.

To examine the accumulation of autoantibodies and immune complexes in the kidneys following the overexpression of MYC, kidneys were obtained from a wild type mouse (A) or an Eµ-MYC/BCR$^{HEL}$/sHEL mouse (B) for histological examination. The tissues were sectioned and stained with hematoxylin and eosin, and microscopic images were obtained. The magnification was 100×. For immununofluorescence, kidneys were obtained from a wild type mouse (C) or an Eµ-MYC/BCR$^{HEL}$/sHEL mouse (D). Frozen tissues were sectioned and stained with Rhodamine conjugated antibodies to IgM. The magnification was 5×. The results presented in FIG. 4 (lower panel) show the accumulation of autoantibodies and immune complexes in the kidneys following the overexpression of MYC.

We have observed that mice that would otherwise be tolerant to a transgenic auto-antigen mounted an immune response to the antigen if MYC was singly expressed in the B-cell lineage. The responsive B-cells converted to an activated phenotype and produced autoantibody that engendered immune complex disease of the kidney. MYC was required to both establish and maintain the breach of tolerance. These mice also developed lymphomas, most likely as a result of cooperation between signals derived from BCR and MYC. These effects may be due to the ability of MYC to serve as a surrogate for cytokines. We found that MYC could mimic the effects of cytokines on both B-cell proliferation and survival, and indeed, was required for those effects. Our data suggest that MYC overexpression is required to establish and maintain the breach of immunological tolerance.

The ability to immortalize self-reactive B-cells that overexpress MYC, in an antigen dependent manner allows the stabilization of many more specificities than traditional approaches for the generation of hybridoma cell lines, due to no longer being limited by the short lifespan of tolerant B-cells, and no longer requiring anergic B-cells to enter cycle to productively fuse with myeloma cell lines.

Example 4

The following example demonstrates the use of B-cell specific, Dox-regulated MYC-overexpressing mice to generate B-cell lines from autoreactive backgrounds.

Figure 4:
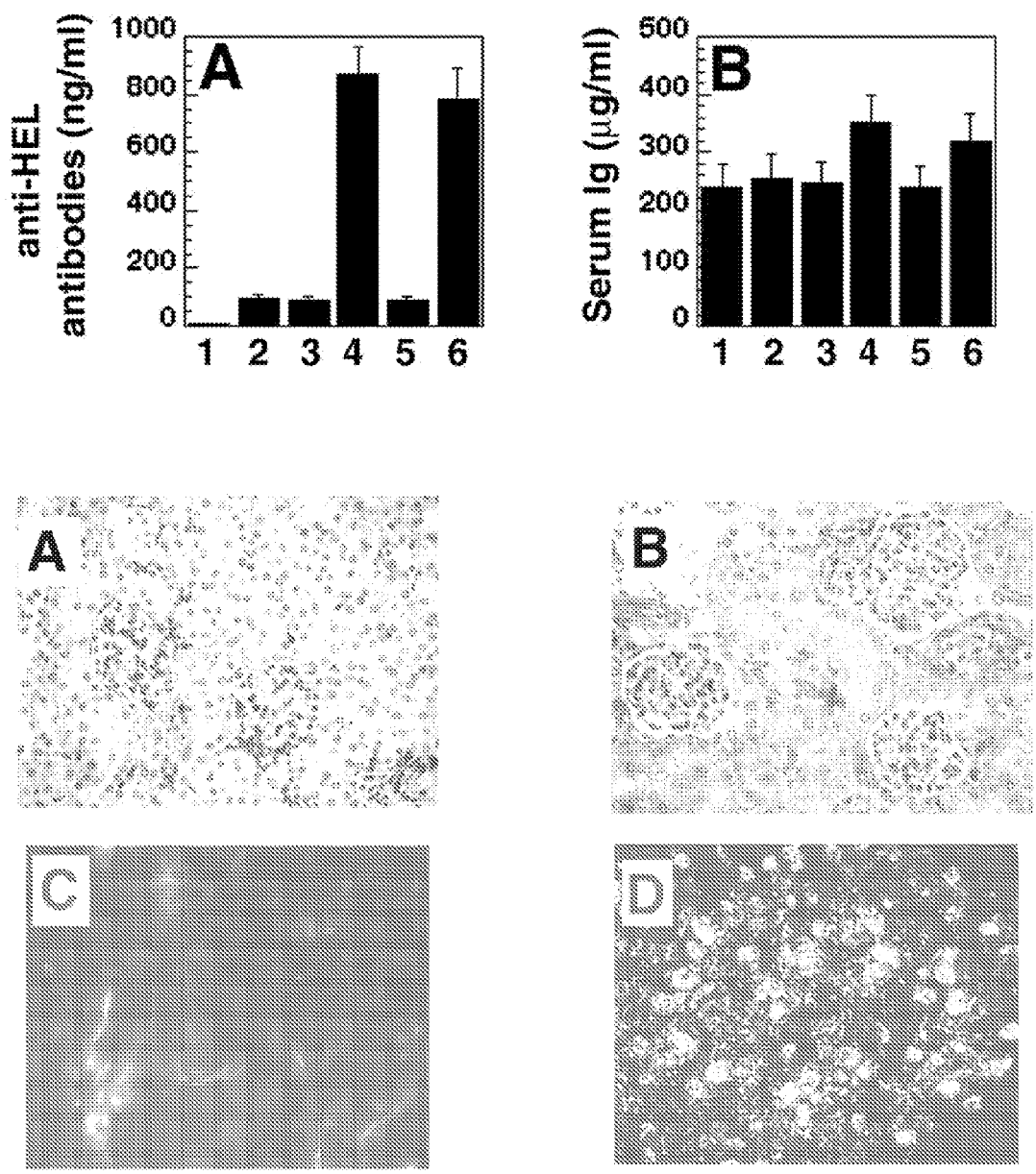
FIG. 4 shows the accumulation of autoantibodies in serum following the overexpression of MYC (top panel) and the accumulation of autoantibodies and immune complexes in the kidneys following the overexpression of MYC (bottom panel).

The results presented above show that a surfeit of MYC is able to break B-cell tolerance to a soluble autoantigen. In those studies, MYC-overexpressing BCR$^{HEL}$ transgenic B-cells could mount a vigorous response to sHEL and engender a polyclonal autoimmune lymphoprolifeative disease prior to the onset of a malignancy (FIGS. 3 and 4). Our studies also indicate that the overexpression of MYC in autoreactive B-cells is able to render the B-cells independent of T-cell help, through MYC's abilities to provide proliferative and survival signals. The expanded population of MYC-overexpressing, autoreactive B-cells went on to generate a B-cell lymphoma that remained dependent upon both continuous exposure to its cognate antigen and overexpression of MYC. We were able to harvest the B-cells from the lymph nodes, spleens and bone marrows from the tumor-bearing mice and were able to establish many cell lines that expressed the BCR$^{HEL}$ transgene and secreted anti-HEL IgM, without fusing the primary cells to a myeloma fusion partner.

We have been able to obtain similar results using two additional circumstances. In one case, we crossed the Ars/A1 mouse to the Eµ-MYC strain. Those mice (n=9 mice) developed a Burkitt's like lymphoma on average at 36 days of age. The tumors were composed of mature, activated B-cells. Those cells expressed IgM on their surface. Those results demonstrate the ability of MYC overexpression to break tolerance for autoreactive B-cells in the context of a low-affinity, anti-DNA antibody. The second instance used MMTV-rtTA/TRE-MYC mice. Those mice enable the B-cell specific, temporally regulated overexpression of MYC following the withdrawal of doxycycline from the diet of those bigenic mice. When we withdrew the mice from the doxycycline containing diet at four months of age, they accumulated activated peripheral B-cells, anti-nuclear antibodies in their serum, immune complex deposition in their kidneys and developed B-cell lymphomas within 6 weeks (average instance was 42 days). We have been able to establish cell lines from those tumors without fusion to a myeloma partner cell. These results suggest a use of this system as a novel approach to generate B-cell lines that express autoreactive B-cell receptors.

Example 5

The following example demonstrates that antibodies produced in MYC-overexpressing mice function in vivo.

In order to examine whether the HEL-specific antibodies that we generated in MMTV-tTA/TRE-MYC mice could function in vivo, we decided to use a model of lethal viral infection. Porcine Rabies Virus (PRV) is a member of the alpha-herpes viruses that has been previously shown to be lethal in mice following intravenous administration. We constructed two variants of PRV. In one instance, we fused one of the sequences for a gene called US-9 to GFP. This construct allows for tracking of the virus and virally infected cells in a different setting. Importantly, the US-9 protein is still produced and retains its function. The virus is fully pathogenic in spite of its additional genetic cargo. We also generated a variant of PRV that encodes the open reading frame for HEL. This viral variant was shown to express HEL by western blot analysis of infected cells (not shown).

GFP-expressing virus or the HEL-expressing virus inoccula (200 µl of viral supernatants containing a titer of $10^9$ PFU) were incubated with HEL-specific antibodies diluted 1:500 for one hour, on ice. The mixtures were then injected intravenously into cohorts of four mice. The mice were then monitored for four days following administration of the virus and antibody mixtures and euthanized when they exhibited severe neurological clinical signs associated with PRV infection.

Figure 5:
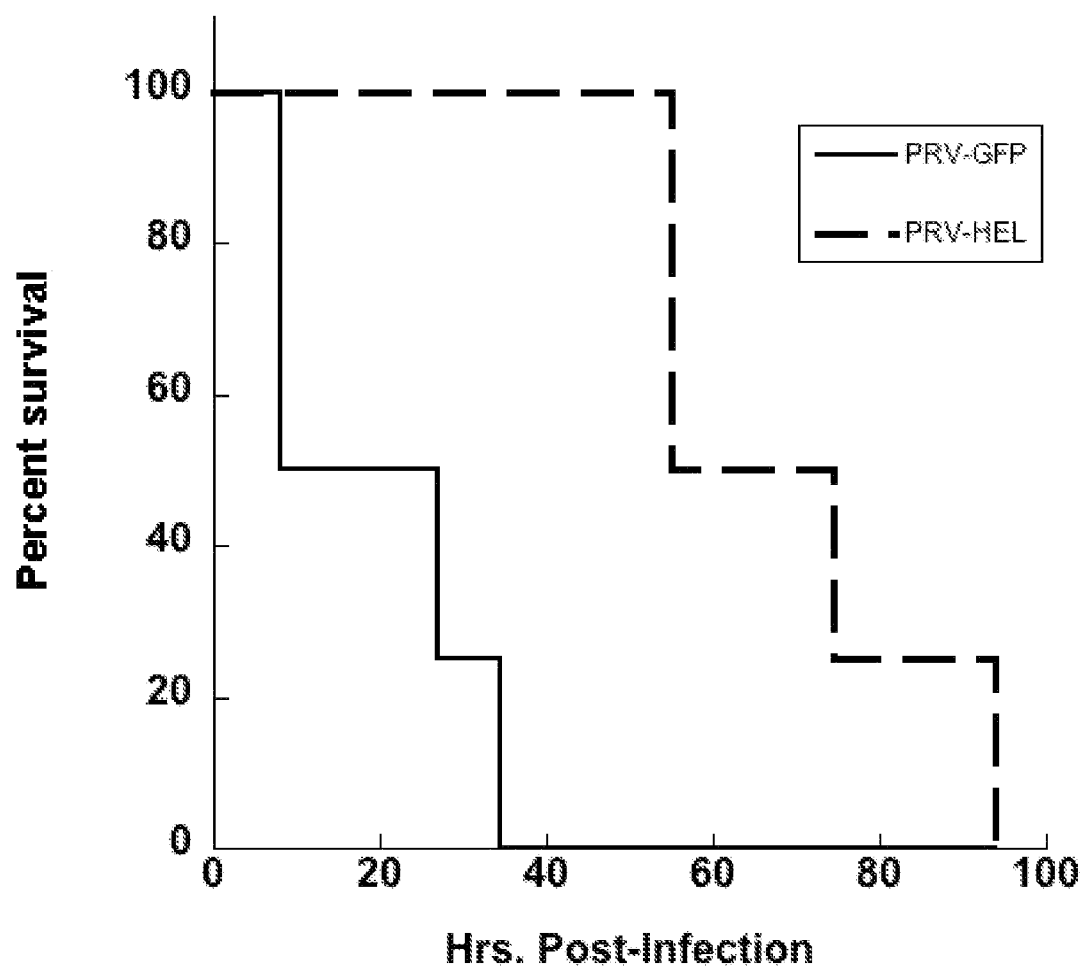
FIG. 5 shows the protection of mice with novel HEL-specific antibodies from lethal challenge of PRV variants that express HEL.

As shown in FIG. 5, the GFP-expressing virus (solid line) was not affected by the presence of HEL-specific antibodies. The kinetics of mortality in that cohort were comparable with our previous experience with wild type PRV strains. In contrast, the kinetics of mortality in the mice that received the HEL-expressing virus (dashed line) were significantly delayed and that cohort of mice lived for almost twice as long as the mice injected with the GFP-expressing virus. The viruses used for these experiments only expressed the US-9 fusion protein transiently. After entry into cells, they produce wild type PRV. The delay in mortality suggests the ability of the antibodies to inhibit viral infection.

Example 6

The following example demonstrates the development of novel antibodies to infectious agents using H5N1 as a prototype.

In order to test the ability of the MMTV-tTA/TRE-MYC mice to generate novel antibodies to antigens of interest through the introduction into the system as neo-self antigens, an approach that relies on the generation of retroviral bone marrow chimaeric mice was used. The coding region of hemmaglutinin (HA) (the ORF encoding portion of the cDNA—no untranslated portions were present in the clone) from the A/Ty/Ont/7732/66 (H5N9) isolate was subcloned into pMIG in order to generate pMISCV-H5-IRES-GFP (pMIG-H5). Bone marrow from 5-FU treated TRE-MYC mice was transduced with pMIG-H5 and pMIG-tTA. Approximately 60% of the cells were transduced as determined by flow cytometric analysis of GFP expression. After 3 days, the cells were transplanted into a cohort of lethally irradiated (800/400R) mice (Bl/6 recipients).

The bone marrow chimaeric mice were maintained on SEPTRA and observed daily for externally evident clinical signs of hematological malignancies. 6 weeks post reconstitution, several mice began to show clinical signs of tumor development including hunched posture, ruffled fur, externally palpable tumors (splenomegaly and lymphadenopathy) and rapid breathing. Between 7-8 weeks post reconstitution, 100% of the mice exhibited signs of tumor development. Mice were sacrificed and analyzed by fluorescent microscopy for evidence of GFP expression. 100% of the sacrificed mice had splenomegaly and GFP expression in the lymph nodes, bone marrow and spleen.

Figure 6:
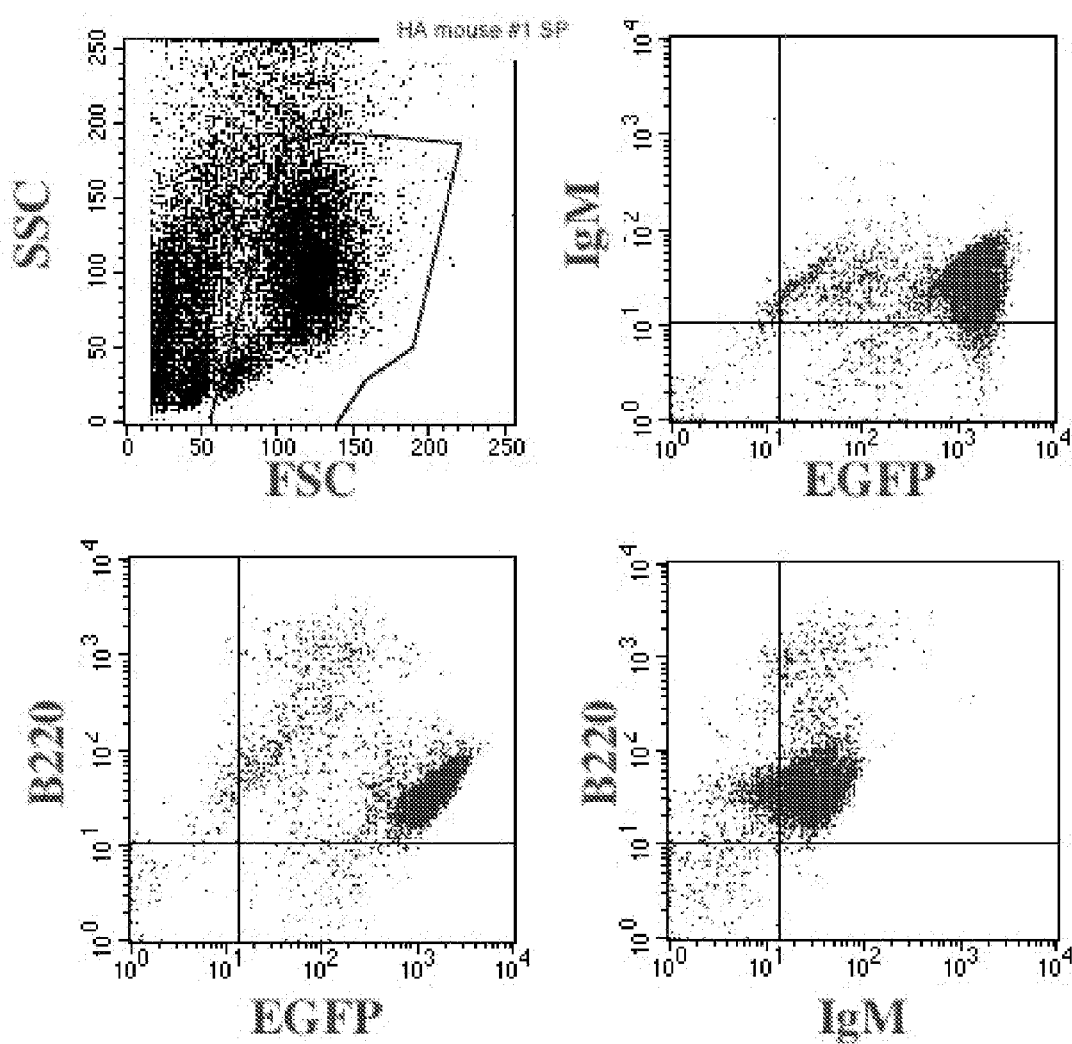
FIG. 6 shows the surface phenotype of B-cell tumors developed in retroviral chimaeric mice.

Lymph nodes and spleen were collected and used to generate a single cell suspension that was plated into 24 well plates. The remaining cells were either cultured to begin to generate cell lines, or cryopreserved for subsequent analysis. The cells were stained with antibodies specific for the B-cell markers B220 and IgM and analyzed by flow cytometry for expression of the same. FIG. 6 shows that the GFP positive cells express both of the B-cell markers B220 and IgM. The tumors were composed of mature, activated (blasting) B-cells (similar to what are observed in mouse models of Burkitt's lymphoma) that yielded MYC-driven, antigen dependent tumors composed of mature, activated B-cells. These cells were placed in culture and clonally expanded populations were passed starting 8 days after initial seeding. This is a significantly faster timeline than what is normally achieved with current approaches to monoclonal antibody production. In addition, the accelerated time frame by which this novel approach has allowed us to generate novel antibodies to hemagglutinin should render this approach as a rapid response platform for the development of novel neutralizing antibodies to new and emerging infectious diseases and other biological threats. Bone marrow cells can also be frozen to reconstitute large cohorts of mice in the future to further steer specificity or add additional antigens.

Figure 7:
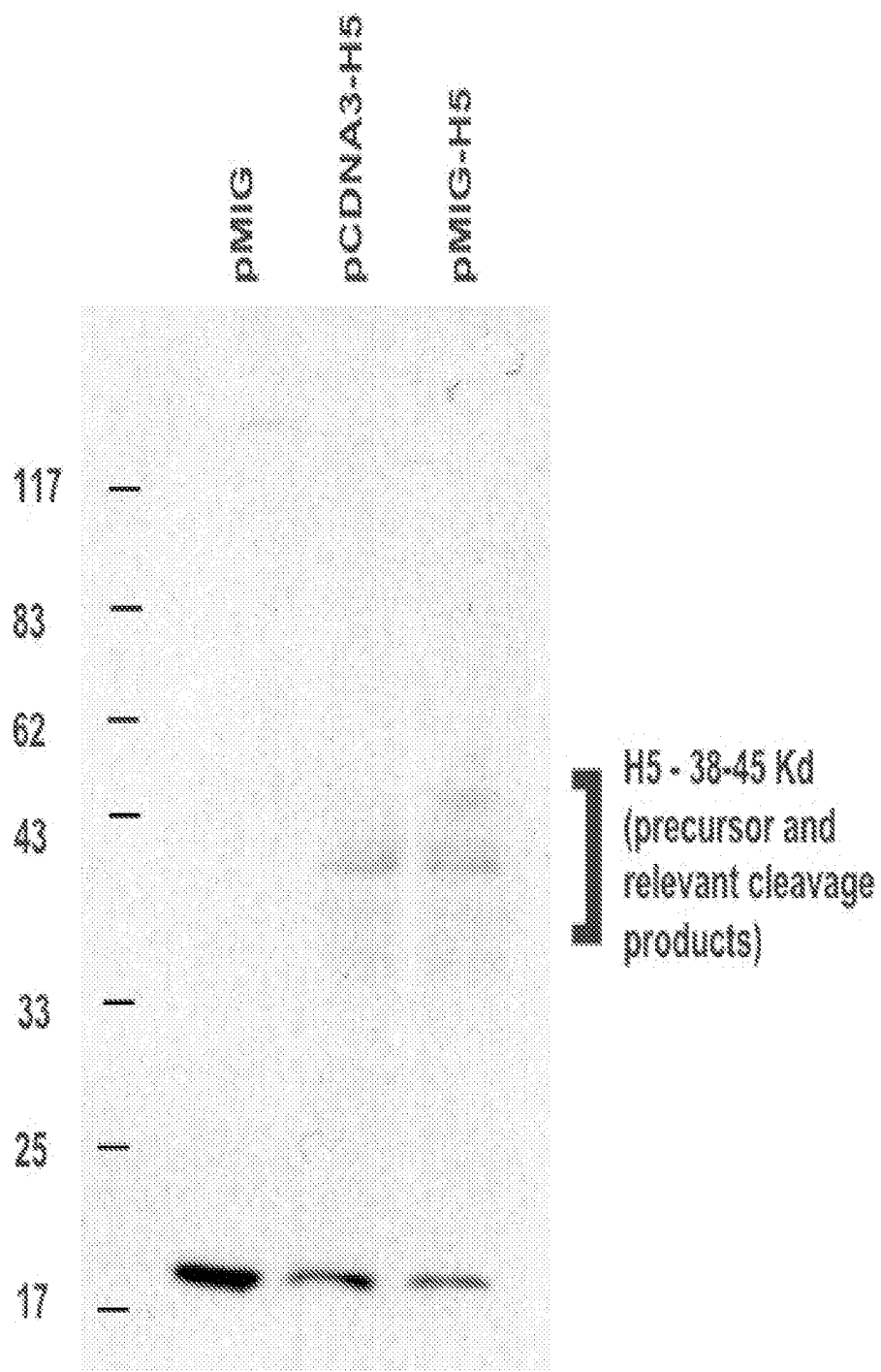
FIG. 7 shows a Western Blot analysis demonstrating the reactivity of serum obtained from retroviral chimaeric mice with HA-expressing cell lysates.

Serum was collected at time the organs were harvested from the mice and stored at −20° C. To determine if the tumors were generating antibodies against the H5 HA protein, the serum was used at 1:5000 dilution in Western blot analyses. Protein lysates (Triton X-100 based lysis buffer) from 293 cells transfected with pMIG-HA, a plasmid expressing the HA from the A/Ty/Ont/7732/66 isolate, or the positive control plasmid pCDNA3-H5 were separated by SDS-PAGE (12% gel), transferred to a PVDF membrane, and the membrane was probed with the diluted serum followed by incubation with HRP conjugated secondary antibody. FIG. 7 shows that serum from tumor-bearing mice reacts with HA from 293 cells expressing either pMIG-HA (center lane) or the positive control plasmid pCDNA3-H5 (right lane), but did not react with lysates from untransfected 293 cells or lysates from cell transfected with pMIG vector alone (left lane).

HA protein appears as an approximately 38-40 kD band. The lower molecular weight band (19 Kd) appears non-specific and serves as a good loading control. The banding pattern that developed is consistent with H5 and the cleavage products that develop during its normal maturation and processing in a cell. The mature HA is composed of two subunits (HA1 and the HA2). The HA1 subunit (~40 kDa) forms the globular head of the molecule and is responsible for binding to the host cell sialic acid receptors on surface glycoproteins and glycolipids. The HA2 subunit (~20 kDa) subunit is responsible for fusion of the viral envelope with the endosomal membranes of the host cell during entry. A protease cleavage site separates these two subunits and cleavage by host protease is required for entry into the host cell. The vast majority of virus-neutralizing epitopes are found in the HA1 subunit and inhibit virus-receptor interaction.

Figure 8:
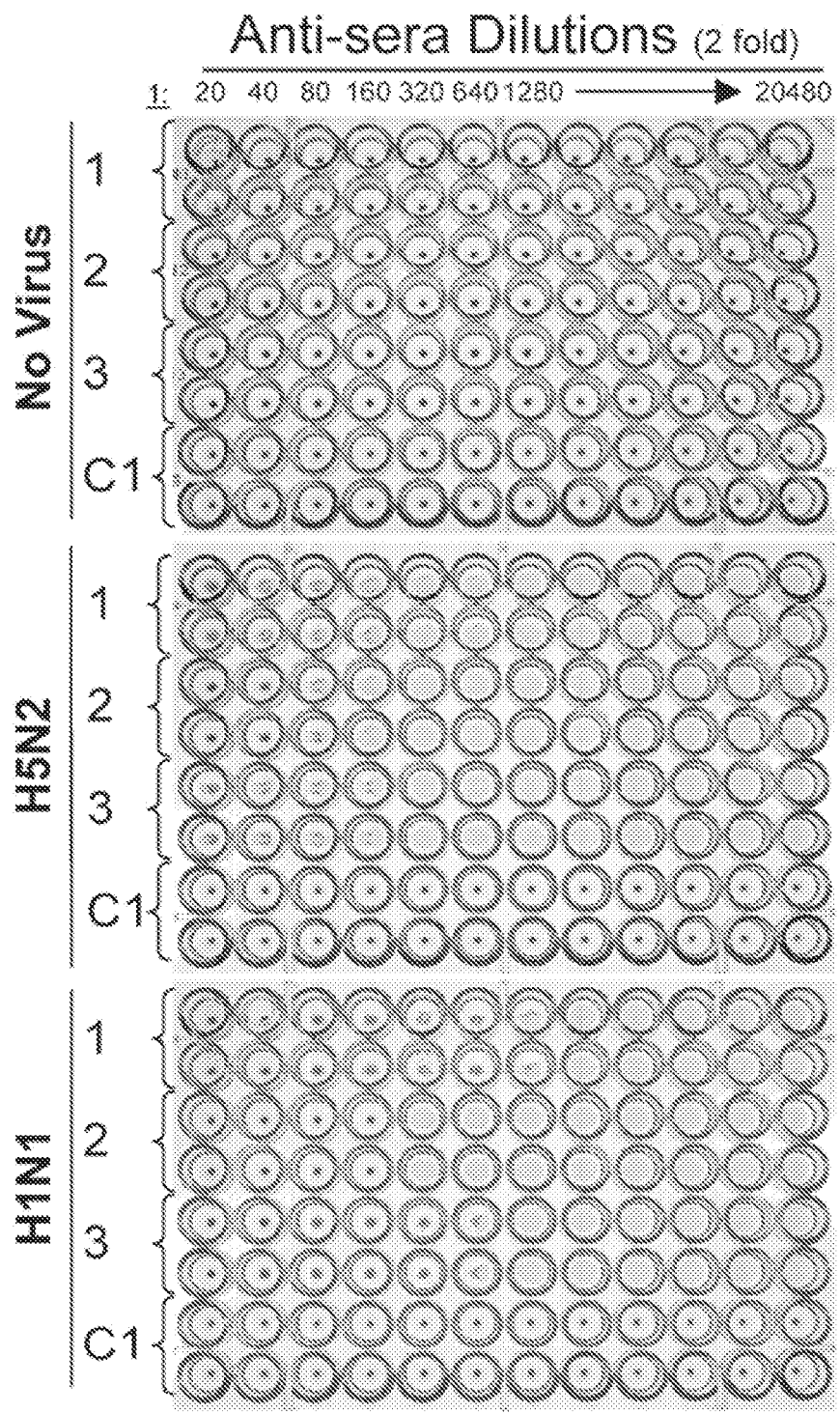
FIG. 8 shows a hemagglutination inhibition analysis of mouse serum obtained from retroviral chimaeric mice.

To test the ability of the sera to block virus-receptor interaction, a hemagglutination inhibition and virus neutralization assay with a variety influenza A isolates including H5N2, H1N1, H7N2, H3N2, and H6N8 subtypes was used (FIG. 8). Sera isolated from three mice (1-3), 6 to 8 weeks after H5/tTA BM transduction, or phosphate buffered saline [PBS] (C1) was diluted serially across microtiter plates in duplicate wells. Following serial dilution, 4 agglutinating units of influenza A viruses A/Mal/WI/944/82 (H5N2), A/NY/1469/02 (H1N1), or PBS (No virus) were added to each well and incubated for 30 minutes. Next, turkey red blood cells were added and incubated for 30 minutes to detect hemagglutination activity. The first column contains a final serum concentration of 1:20.

These data show that the novel antibodies generated to H5N1 were also able to neutralize viruses from a different Glade (H1N1). This suggests that the new approach using the overexpression of MYC is able to unveil virally encoded epitopes that are normally ignored, since they likely mimic self-proteins and tolerance mechanisms prevent good responses to those residues. This may allow one to identify and therapeutically exploit common residues among different viruses of a specific type (influenza, or other types).

Cell lines from lymph node and spleen cells can be created and the supernatants can be tested for reactivity with HA to demonstrate that cell lines producing antibodies against the HA protein can be generated. These supernatants and/or serum can also be tested for the ability to neutralize H5 containing influenza viruses. The neutralizing assays can include a measure of whether an antibody can inhibit an agglutination assay, using flu viruses and sheep red blood cells, as well as effective infection of epithelial cells in vitro, or mice in vivo.

Additional disclosure and embodiments of the present invention can be found in the attached manuscript, which is incorporated herein by reference in its entirety.

While various embodiments of the present invention have been described in detail herein, it is apparent that modifications and adaptations of those embodiments will occur to those skilled in the art. It is to be expressly understood, however, that such modifications and adaptations are within the scope of the present invention, as set forth in the following claims:

We claim:

1. A method for producing an antibody to an antigen comprising:
 a) providing a non-human mammal that inducibly overexpresses MYC, wherein the non-human mammal was produced by
 transferring a mammalian hematopoietic stem cell into the non-human mammal, wherein the mammalian hematopoietic stem cell comprises a recombinant nucleic acid molecule encoding an inducible MYC and a recombinant nucleic acid molecule encoding an antigen, and wherein the non-human mammal was lethally-irradiated or sub lethally-irradiated prior to having the hematopoietic stem cell transferred into the non-human mammal;

b) inducing the overexpression of MYC in the non-human-mammal after formation of mature B cells from the transferred mammalian hematopoietic stem cell;

c) recovering a B cell overexpressing MYC from the non-human mammal, wherein the B cell comprises the recombinant nucleic acid molecule encoding the inducible MYC and the recombinant nucleic acid molecule encoding the antigen;

d) culturing the B cell overexpressing MYC under conditions in which MYC overexpression is maintained; and e) recovering the antibody from the B cell culture.

2. The method of claim 1, wherein the antigen comprises a human antigen.

3. The method of claim 1, wherein the inducible MYC is MYC-ER.

4. The method of claim 3, wherein MYC-ER is induced by 4-hydroxytamoxyfen (4OHT).

5. The method of claim 1, wherein the B-cell overexpressing MYC is recovered from the spleen or a lymph node.

6. The method of claim 1, wherein the hematopoietic stem cell is a human hematopoietic stem cell.

7. The method of claim 6, wherein the antibody is a human antibody.

8. The method of claim 1, wherein the antigen is selected from the group consisting of a viral antigen, a fungal antigen, a bacterial antigen, a helminth antigen, a parasitic antigen, an ectoparasite antigen, a protozoan antigen, an antigen associated with a disease, and an antigen associated with a condition.

9. The method of claim 1, wherein the antigen is selected from the group consisting of a protein, a peptide, a cellular receptor, and carbohydrate.

10. The method of claim 1, wherein the antibody is a monoclonal antibody.

11. The method of claim 1, wherein the hematopoietic stem cell is a transgenic hematopoietic stem cell.

12. The method of claim 1, wherein the hematopoietic stem cell is a recombinantly transduced hematopoietic stem cell.

* * * * *